United States Patent [19]
Jönsson et al.

[11] Patent Number: 5,382,600
[45] Date of Patent: Jan. 17, 1995

[54] 3,3-DIPHENYLPROPYLAMINES AND PHARMACEUTICAL COMPOSITIONS THEREOF

[75] Inventors: Nils A. Jönsson, Södertälje; Bengt A. Sparf, Trångsund; Lembit Mikiver, Järna; Pinchas Moses, Saltsjö-Boo; Lisbet Nilvebrant, Bromma; Gunilla Glas, Spånga, all of Sweden

[73] Assignee: Pharmacia Aktiebolag, Uppsala, Sweden

[21] Appl. No.: 810,185

[22] Filed: Dec. 19, 1991

Related U.S. Application Data

[63] Continuation of Ser. No. 543,767, Sep. 24, 1990, abandoned.

[30] Foreign Application Priority Data

Jan. 22, 1988 [SE] Sweden .................. 8800207-6

[51] Int. Cl.6 .............. A61K 31/135; A61K 31/165; A61K 31/18; C07C 217/62
[52] U.S. Cl. .................. 514/603; 514/620; 514/648; 564/86; 564/165; 564/316
[58] Field of Search ............. 564/86, 165, 316; 514/603, 620, 648

[56] References Cited

U.S. PATENT DOCUMENTS 3,446,901 5/1969 Jones .................. 424/330

FOREIGN PATENT DOCUMENTS 111894 3/1969 Denmark .
1169944 11/1969 United Kingdom .
1169945 11/1969 United Kingdom .

OTHER PUBLICATIONS

Markaryan et al., Chemical Abstracts, vol. 97 (1982) 120105n.

Atwal et al., J. Med. Chem., vol. 30 (1987) pp. 627–365.
Strehlke et al., Chemical Abstracts, vol. 91 (1979) 107943r.

Primary Examiner—Richard L. Raymond
Attorney, Agent, or Firm—Pollock, Vande Sande & Priddy

[57] ABSTRACT

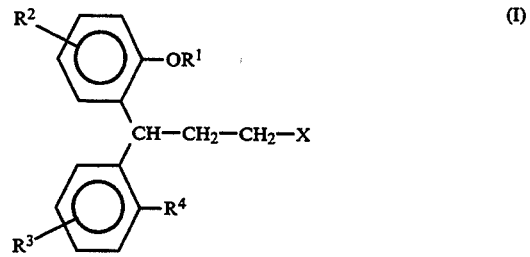

Novel 3,3-diphenylpropylamines of formula (I) wherein $R^1$ signifies hydrogen or methyl, $R^2$, $R^3$ and $R^4$ independently signify hydrogen, methyl, methoxy, hydroxy, carbamoyl, sulphanoyl or halogen, and X represents a tertiary amino group $-NR^5$, $R^6$, wherein $R^5$ and $R^6$ signify non-aromatic hydrocarbyl groups, which may be the same or different and which together contain at least three carbon atoms, and which may form a ring together with the amine nitrogen, their salts with physiologically acceptable acids and, when the compounds can be in the form of optical isomers, the racemic mixture and the individual enantiomers, their use as drugs, especially as anticholinergic agents, their use for preparing an anticholinergic drug, pharmaceutical compositions containing the novel amines, and methods for preparing the same.

7 Claims, No Drawings

3,3-DIPHENYLPROPYLAMINES AND PHARMACEUTICAL COMPOSITIONS THEREOF

This is a continuation of Ser. No. 07/543,767, filed on Sep. 24, 1990, now abandoned.

The present invention relates to novel 3,3-diphenylpropylamino derivatives, to pharmaceutical compositions containing the same, and to the use of said derivatives for preparing drugs.

Swedish Pat. No. 215 499 discloses certain 3,3-diphenylpropylyamines having an advantageous effect on the heart and circulation. These pharmacologically active 3,3-diphenylpropylamines are secondary amines. Said Swedish patent also discloses certain chemical intermediates which are tertiary amines carrying aromatic substituents on the amine nitrogen. Neither the end products (secondary amines) nor the intermediates (tertiary amines) have any hydroxy or methoxy groups as substituents in the ortho positions of the phenyl rings, but only meta and para substituents are specifically disclosed.

It is known that terodiline, a commercially available drug having the chemical formula

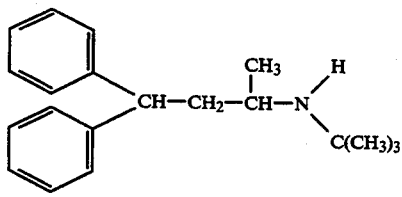

has anti-cholinergic properties, and is well resorbed in the body. However, this drug has a very long biological half-life and it is a multi-effect drug also having other pharmacological properties such as Ca-antagonist, nor-adrenaline antagonist and anti-histamine properties as well as a pronounced effect on the heart.

U.S. Pat. No. 3,446,901, GB-A-1.169.944 and GB-A-1.169.945 disclose certain 3,3-diphenylpropylamine derivatives and pharmaceutical compositions having anti-depressant activity, i.a. N,N-dimethyl-3-(2-methoxyphenyl)-3-phenylpropylamine, which is considered to be the closest prior art as regards chemical structure (see also the comparative tests reported at the end of this specification). DK-A-111.894 discloses a special process for preparing certain diphenylalkylamines having an effect on the heart and circulation. The specifically described compounds are primary or secondary amines, and none of them has any hydroxy or alkoxy substituent in ortho position of the phenyl rings. C.A. Vol. 97(1982) 120105n discloses certain N-arylaklylisoquinolines which may have a hydroxy substituent in the ortho position of a phenyl ring. These compounds have sympatholytic activity and carry aromatic substituents on the nitrogen atom.

It is object of the present invention to provide a novel class of 3,3-diphenylpropylamines having improved anti-cholinergic properties, especially in relation to the effects on these other systems and acute toxicity.

In a first aspect the invention provides novel 3,3-diphenylpropylamines of formula I

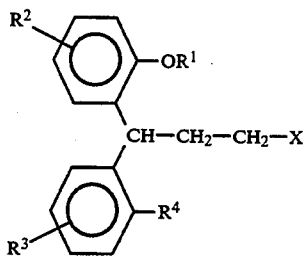

wherein $R^1$ signifies hydrogen or methyl, $R^2$, $R^3$ and $R^4$ independently signify hydrogen, methyl, methoxy, hydroxy, carbamoyl, sulphanoyl or halogen, and X represents a tertiary amino group of formula II

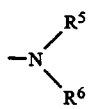

wherein $R^5$ and $R^6$ signifky non-aromatic hydrocarbol groups, which may be the same or different and which together contain at least three carbon atoms, preferably at least four carbon atoms, especially at least five carbon atoms, and where $R^5$ and $R^6$ may form a ring together with the amine nitrogen, said ring preferably having no other hetero atom that the amine nitrogen.

The compounds of formula I can form sales with physiologically acceptable acids, organic and inorganic, and the invention comprises the free bases as well as the salts thereof. Examples of such acid addition salts include the hydrochloride, hydrobromide, hydrogen fumarate, and the like.

When the novel compounds can be in the form of optical isomers, the invention comprises the racemic mixture as well as the individual enantiomers as such.

A preferred sub-class of compounds according to the invention comprises tertiary amines of formula I, wherein each of $R^5$ and $R^6$ independently signifies $C_{1-8}$-alkyl, especially $C_{1-6}$-alkyl, or adamantyl, $R^5$ and $R^6$ together comprising at least three, preferably at least four carbon atoms. $R^5$ and $R^6$ may carry one or more hydroxy groups, and they may be joined to form a ring together with the amine nitrogen atom.

Presently preferred tertiary amino-groups X in formula I include the following groups a)–f), each of which may carry one or more hydroxy groups.

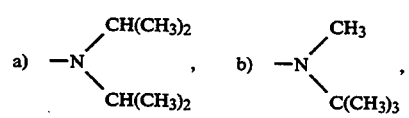

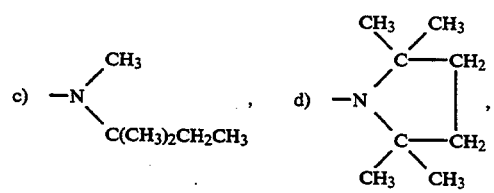

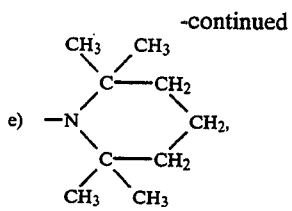

e)

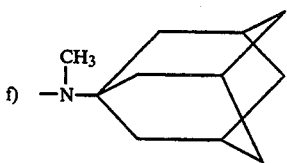

f)

The following are examples of presently preferred specific compounds of formula I:

N,N-diisopropyl-3-(2-hydroxy-5-methylphenyl)-3-phenylpropylamine and its (+)-isomer, N-methyl-N-tert.butyl-3-(2-hydroxyphenyl)-3-phenylpropylamine, N-methyl-N-tert.butyl-3-(2,4-dihydroxyphenyl)-3-phenylpropylamine, N-methyl-N-tert.butyl-3,3-bis-(2-hydroxyphenyl)-propylamine, N,N-diisopropyl-3,3-bis-(2-hydroxyphenyl)propylamine, N,N-diisopropyl-3-(2,5-dihydroxyphenyl)-3-phenylpropylamine, N-methyl-N-tert.butyl-3-(2,5-dihydroxyphenyl)-3-phenylpropylamine, N,N-diisopropyl-3-(2-methoxyphenyl)-3-phenylpropylamine, N-(3-(2-methoxyphenyl)-3-phenylpropyl)-2,2,6,6-tetramethylpiperidine In a second aspect the invention provides methods for preparing the compounds of formula I, especially the following methods:

a) reacting a reactively esterified 3,3-diphenylpropanol of formula III

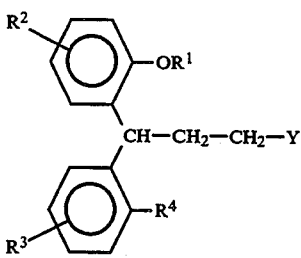

III wherein $R^1$-$R^4$ are as defined above, and any hydroxy groups may be protected such as by methylation or benzylation, and wherein Y is a leaving group, preferably halogen or an alkyl or arylsulphonyloxy group, with an amine of formula IV H—X  IV wherein X is as defined above, or b) reducing a 3,3-diphenylpropionamide of formula V

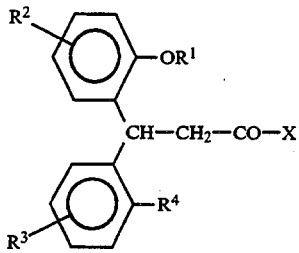

V wherein $R^1$-$R^4$ and X are as defined above and any hydroxy groups may be protected, preferably using a complex metal hydride, c) N-methylating a secondary 3,3-diphenylpropylamine VI

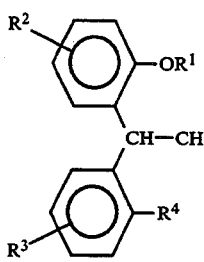

VI wherein $R^1$-$R^4$ are as defined above and any hydroxy groups may be protected, and wherein Z has the same meaning as $R^5$ and $R^6$ with the exception of methyl, Z preferably being a hydrocarbyl group comprising at least three carbon atoms, the N-methylation preferably being carried out using formaldehyde or formic acid, or d) reducing a 3,3-diphenylpropylamine of formula VIIa or VIIb

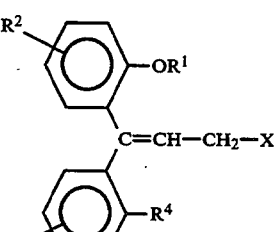

VIIa

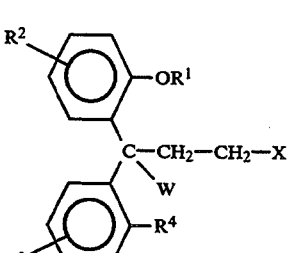

VIIb wherein $R^1$-$R^4$ and X are as defined above and any hydroxy groups may be protected, and W signifies a hydroxy group or a halogen atom, preferably by means of catalytic hydrogenation, and i) when necessary splitting off hydroxy protecting groups in the compounds obtained, if desired after mono or di-halogenation of one or both of the phenyl rings, and/or ii) if desired converting obtained bases of formula I into salts thereof with physiologically acceptable acids, or vice versa, and/or iii) if desired separating an obtained mixture of optical isomers into the individual enantiomers, and/or iv) if desired methylating an ortho-hydroxy group in an obtained compound of formula I, wherein $R^1$ is hydrogen and/or $R^4$ is hydroxy.

The above general methods can be carried out in a manner known per se and/or in accordance with the working examples described below, with due consideration of the desired amino groups and the substituents on the benzene rings.

The removal of hydroxy protecting groups according to i) above can e.g. be done by treatment with hydrobromic acid, borontribromide or by catalytic hydrogenation.

The separation of mixtures of optical isomers, according to ii) above, into the individual enantiomers can e.g. be achieved by fractional crystallization of salts with chiral acids or by chromatographic separation on chiral columns.

Novel compounds of formula VIII

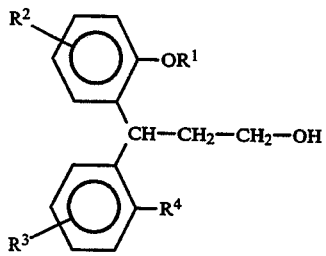

VIII wherein $R^1$–$R^4$ are as defined above, and the corresponding protected compounds (e.g. comprising protected hydroxy groups), are useful as chemical intermediates for the preparation of e.g. the compounds of formula I, and they can be prepared by means of several different methods which are known per se, such as by addition of ethylene oxide (X) to a correspondingly substituted diphenylmethane (IX) in the presence of a suitable base such as sodium amide:

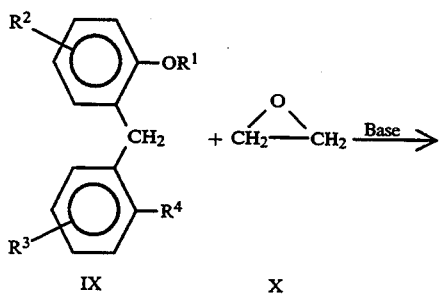

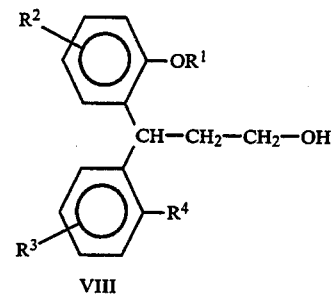

VIII

The compounds VIII can also be prepared by reduction of the corresponding 3,3-diphenylpropionic acids, preferably using complex metal hydrides.

The 3,3-diphenylpropanols VIII can conveniently be converted into the corresponding reactively esterified derivatives III in a manner known per se by displacing the hydroxy groups with e.g. a halogen atom or an alkyl or arylsulphonyloxy group.

The 3,3-diphenylamides of formula V used as starting materials in method b), can e.g. be prepared by reacting the above mentioned 3,3-diphenylpropionic acids with an appropriate amine.

The secondary amines used as starting materials in method c) can conveniently be prepared by reacting a primary amine $H_2N$-Z (wherein Z is as defined above) with a corresponding reactively esterified 3,3-diphenylpropanol in analogy with method a) above, or by reduction of the corresponding secondary 3,3-diphenylpropionamides in analogy with method b) above. The secondary amines can also be prepared by reduction of unsaturated hydroxyamines XI

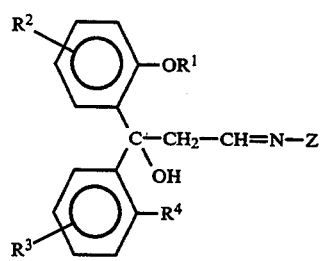

XI wherein $R^1$–$R^4$ and Z are as defined above, either in one step by catalytic hydrogenation, or by reduction to the corresponding saturated hydroxyamine, preferably using a complex metal hydride such as lithium aluminium hydride, followed by removal of the hydroxy group by catalytic reduction. As an alternative, the hydroxy group may first be split off as water, followed by reduction of the formed unsaturated amine.

The unsaturated hydroxy amines XI can conveniently be prepared by the addition of a Schiff base of formula XII

$CH_3$—CH=N—Z    XII wherein Z is as defined above, to a benzophenone of formula XIII

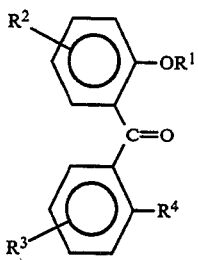

XIII wherein $R^1$-$R^4$ are as defined above, in the presence of a base, preferably a lithium organic base such as lithium diisopropylamide.

Also the starting materials VIIa, VIIb for process d) can be prepared by methods known per se, such as by addition of an organometallic compound XIVa or XIVb

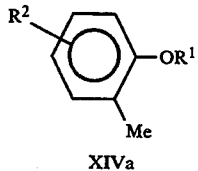 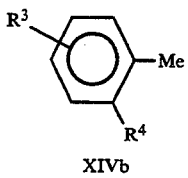

XIVa           XIVb to a ketoamine XVa or XVb respectively to form a corresponding hydroxy amine XVI

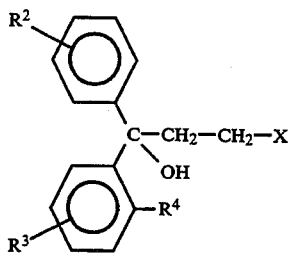

XVI and, if desired, splitting off water from compound XVI.

In formulae XIVa, XIVb, XVa, XVb, XVI, $R^1$-$R^4$ are as defined above, and Me signifies a metal such as magnesium or lithium.

In accordance with the invention the compounds of formula I, in the form of free bases or salts with physiologically acceptable acids, can be brought into suitable galenic forms, such as compositions for oral use, for injection, or the like, in accordance with accepted pharmaceutical procedures. Such pharmaceutical compositions according to the invention comprise the compounds of formula I in association with compatible pharmaceutically acceptable carrier materials, or diluents, as is well known in the art. The carriers may be any inert material, organic or inorganic, suitable for enteral, percutaneous or parenteral administration such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmaceutically active agents, and conventional additives such as stabilizers, wetting agents, emulsifiers, flavouring agents, buffers, and the like.

The compositions according to the invention can e.g. be made up in solid or liquid form for oral administration, such as tablets, capsules, powders, syrups, elixirs and the like, in the form of sterile solutions, suspensions or emulsions for parenteral administration, and the like.

The compounds and compositions according to the invention can be used for treating cholin-mediated disorders such as urinary incontinence. As is well known, the dosage depends on several factors such as the potency of the selected specific compound, the mode of administration, the age and weight of the patient, the severity of the condition to be treated, and the like. The daily dosage may, for example, be from about 0.05 mg to about 4 mg per kilo of body weight, administered in one or more doses, e.g. containing from about 0.05 to about 200 mg each.

The invention will be further illustrated by the following non-limiting examples.

General $^1$H-NMR spectra were run in CDCl$_3$ using a JEOL PMX60 spectrometer. In some cases, only a limited number of spectral peaks, useful for characterization purposes, are reported.

Reported yields mostly refer to crude material of sufficient purity to be taken to the next stage.

Solvents are abbreviated as follows:
IPE = diisopropyl ether
PET = petroleum ether
Ether = diethyl ether Amines are abbreviated as follows:
IPA = diisopropyl amine
TBA = tert.butyl amine Melting points were taken on a Koefler bench.
Temperatures are in °C.

Water is used for the washing steps, unless otherwise stated.

EXAMPLE 1

Preparation of 4-phenyl-3,4-dihydrocoumarins a) 4-(2-Methoxy-5-methylphenyl)-6-methyl-3,4-dihydrocoumarin (I)

A mixture consisting of 2-methoxy-5-methylcinnamic acid (96.0 g, 0.5 mol), p-cresol (108 g, 1.0 mol), tetraline (200 ml), and conc. sulphuric acid (20 g) was heated slowly to refluxing temperature (145°–150°). After 1½–2 h, the mixture was cooled, taken up in ether, washed with water and sodium carbonate, dried and evaporated, giving 138 g (97%) crude oil. Two recrystallisations from acetone gave white crystals of the desired lactone, m.p. 126°–127°.

$C_{18}H_{18}O_3$ (282.3) requires: C, 76.57; H, 6.43; O, 17.00, Found: C, 76.9; H, 6.44; O, 17.0.

b) 6-Hydroxy-4-phenyl-3,4-dihydrocoumarin (II) was prepared in a similar way in 97% yield from cinnamic acid and hydroquinone. M.p. 138° (IPE-Ether).

$C_{15}H_{12}O_3$ (240.3) requires: C, 74.99; H, 5.04; O, 19.98, Found: C, 75.0; H, 5.00; O, 19.6.

c) 4-(2-Methoxy-4-methylphenyl)-7-methyl-3,4-dihydrocoumarin was obtained in a similar way from 2-methoxy-4-methylcinnamic acid and m-cresol in 58% yield. M.p. 147°–148° (IPE-acetone).

$C_{18}H_{18}O_3$ (282.3) requires: C, 76.57; H, 6.43; O, 17.00, Found: C, 76.4; H, 6.31; O, 17.2.

The above lactone (90 g, 0.32 mol) in methylene chloride (500 ml) was refluxed with BBr$_3$ (115 g, 0.46 mol) for 24 h, the solution was concentrated, the residue was taken up in ether, the solution was washed with sodium carbonate and water, dried and evaporated, giving 80 g (93%) of a syrup which crystallized on standing. Crystallization from IPE-PET gave white crystals of d) 4-(2-hydroxy-4-methylphenyl)-7-methyl-3,4-dihydrocoumarin (III), m.p. 137°.

$C_{17}H_{16}O_3$ (268.3) requires: C, 76.10; H, 6.01; O, 17.89, Found: C, 76.2; H, 6.30; O, 17.0.

e) 8-Hydroxy-4-phenyl-3,4-dihydrocoumarin (IV) was obtained in a similar way from cinnamic acid and catechol in 18% yield. M.p. 136° (IPE).

$C_{15}H_{12}O_3$ (240.2) requires: C, 74.99; H, 5.04; O, 19.98, Found: C, 75.0; H, 5.01; O, 19.9.

f) 4-(2-Methoxyphenyl)-3,4-dihydrocoumarin (V) was obtained in a similar way in 45% yield from methyl 2-methoxycinnamate and phenol. The crude reaction mixture was contaminated with methyl 3-(4-hydroxyphenyl)-3-(2-methoxyphenyl)-propionate. After removal of this by-product with ice-cold NaOH, the title compound was obtained as an oil of sufficient purity to be taken to the next step.

EXAMPLE 2

Preparation of 3,3-diphenylpropionic acid esters a) Methyl 3-(2-methoxy-4-methylphenyl)-3-phenylpropionate (VI)

7-Methyl-4-phenyl-3,4-dihydrocoumarin (78 g, 0.327 mol) in 150 ml methanol and 150 ml acetone containing methyl iodide (100 g, 0.7 mol) and $K_2CO_3$ (55 g, 0.4 mol) was refluxed for 24 h, filtered, and the solvent was evaporated. The residue was dissolved in ether, the solution was washed with water, dried and evaporated giving 86 g (92%) of a viscous oil.

NMR: δ 6.6–7.2 (m 8H), 4.9 (t 1H), 3.8 (s 3H), 3.5 (s 3H), 3.0 (d 2H), 2.2 (s 3H).

b) Methyl 3,3-bis-(2-methoxyphenyl)-propionate (VII) was obtained in the same way in 96% yield from the lactone (V) of Example 1f), m.p. 84°–87° (IPE).

$C_{18}H_{20}O_4$ (300.4) requires: C, 71.98; H, 6.71; O, 21.3, Found: C, 71.4; H, 6.67; O, 21.6.

c) Methyl 3-(2,3-dibenzyloxyphenyl)-3-phenylpropionate (VIII) was obtained in a similar way in quantitative yield from the lactone (IV) of Example 1e) and benzyl chloride in methanol. In addition to $K_2CO_3$ the reaction mixture also contained some NaI. M.p. 72° (IPE).

$C_{30}H_{28}O_4$ (452.5) requires: C, 79.63; H, 6.24; O, 14.14, Found: C, 79.9; H, 6.15; O, 14.1.

d) Methyl 3-(2-benzyloxyphenyl)-3-phenylpropionate (IX) was obtained in a similar way as a viscous oil in 81% yield from 4-phenyl-3,4-dihydrocoumarin and benzyl chloride.

NMR: δ 7.2 (m 14H), 4.9 (s 2H, t 1H), 3.5 (s 3H), 3.0 (t 2H).

e) Methyl 3-(2-methoxy-5-methylphenyl)-3-phenylpropionate (X) was obtained in a similar way from 6-methyl-4-phenyl-3,4-dihydrocoumarin in 96% yield.

NMR: δ 7.4 (m 8H), 5.0 (t 1H), 3.9 (s 3H), 3.7 (s 3H), 3.2 (d 2H), 2.4 (s 3H).

f) Methyl 3,3-bis-(2-methoxy-5-methylphenyl)propionate (XI) was obtained in a similar way in quantitative yield from the lactone (I) of Example 1a) and methyl iodide.

NMR: δ 6.6–7.1 (m 6H), 5.1 (t 1H), 3.7 (s 6H), 3.5 (s 3H), 3.0 (d 2H), 2.2 (s 6H).

g) Methyl 3-(2,5-dibenzyloxyphenyl)-3-phenylpropionate (XII) was obtained in a similar way in 90% yield from the lactone (II) of Example 1b) and benzyl chloride.

NMR: δ 6.8–7.4 (m 18H), 5.0 (s 4H, t 1H), 3.7 (s 3H), 3.1 (d 2H).

h) Methyl 3,3-bis-(2-benzyloxy-4-methylphenyl)propionate (XIII) was obtained in a similar way in 95% yield from the lactone (III) of Example 1d) and benzyl chloride. By GLC the product is homogenous, and by MS it has the correct M.W.

i) Ethyl 3-(2,4-dimethoxyphenyl)-3-phenylpropionate (XIV)

A mixture of ethyl cinnamate (88 g, 0.5 mol), dimethyl resorcinol (276 g, 2.0 mol) and conc. sulphuric acid (50 g) was stirred on a boiling water-bath for 2 h, whereafter all the volatile material was distilled off in vacuum. The residual oil was dissolved in ether, the solution was washed with sodium carbonate, dried, and evaporated giving 101 g (64%) of the title ester in the form of a viscous oil.

NMR: δ 6.4–7.2 (m 8H), 4.9 (t 1H), 4.0 (q 2H), 3.7 (s 6H), 3.0 (d 2H), 1.1 (t 3H).

j) Methyl 3,3-bis-(2,4-dimethoxyphenyl)propionate (XV) was obtained in a similar way from methyl 2,4-dimethoxycinnamate and dimethyl resorcinol. The product thus obtained contained about 23% of dimethyl resorcinol. It was taken to the next step without further purification.

k) Methyl-3-(5-chloro-2-methoxyphenyl)-3-phenylpropionate

6-Chloro-4-phenyl-3,4-dihydrocoumarin (435 g, 1.68 mol. Preparation: T. Manimaran & V. T. Ramakrishnan, Ind. J. Chem. B 18 (1979) 328) is added to a hot solution of sodium hydroxide (140 g, 3.5 mol) in water (500 ml). The solution is chilled to 25° C. and dimethyl sulphate (442 g, 3.5 mol) is added dropwise during 1 h with stirring and cooling at 25°–35° C. The mixture is stirred for an additional 2 h whereupon a solution of 100 g of sodium hydroxide in 500 ml of water is added and the mixture is stirred until a clear solution is obtained. An excess of concentrated hydrochloric acid is added to precipitate the methoxy acid, which separates as an oil which slowly crystallizes. It is filtered off, washed with water and dried. Crystallization from 2-propanol gives colourless crystals of 3-(5-chloro-2-methoxyphenyl)-3-phenyl propionic acid, m.p. 144° C. Yield 455 g.

The above acid (291 g, 1.0 mol) in 1 liter methanol containing 50 g concentrated sulphuric acid was refluxed for 8 h. The solvent was distilled off, the residue was taken up in ether, washed with water and sodium carbonat solution, dried and evaporated giving 300 g (100%) crude oil. Recrystallisation from IPE gave white crystals of the title compound, m.p. 65°–66°.

$C_{17}H_{17}ClO_3$ (304,8) requires: C, 67.0; H, 5.62; Cl, 11.63, Found: C, 68.1; H, 5.82; Cl, 11.7.

EXAMPLE 3

Preparation of 3,3-diphenylpropanols a) 3-(2-Methoxy-4-methylphenyl)-3-phenylpropanol (XVI)

The ester (VI) of Example 2a) (84 g, 0.295 mol) in 150 ml dry ether was added dropwise to a suspension of LiAlH$_4$ (11.3 g, 0.295 mol) in 300 ml dry ether. The mixture was stirred overnight, then decomposed by the careful addition first of 11 g of water, then of 15% NaOH until a white granular precipitate was formed. The mixture was filtered, the filtrate was washed with water, dried, and evaporated giving 71 g (91%) of an oil which crystallized on standing. Recrystallization from IPE-PET gave white crystals, m.p. 83°.

$C_{17}H_{20}O_2$ (256.4) requires: C, 79.65; H, 7.88; O, 12.48, Found: C, 79.4; H, 7.89; O, 12.7.

b) 3,3-Bis-(2-methoxyphenyl)propanol (XVII) was obtained in a similar manner in quantitative yield as a viscous oil from the ester (VII) of Example 2b).

c) 3-(2,3-Dibenzyloxyphenyl)-3-phenylpropanol (XVIII) was obtained in a similar way as a viscous oil in 96% yield from the ester (VII) of Example 2c).

d) 3-(2-Benzyloxyphenyl)-3-phenylpropanol (XIX) was obtained in a similar was as an oil in 78% yield from the ester (IX) of Example 2d).

e) 3-(2-Methoxy-5-methylphenyl)-3-phenylpropanol (XX) was obtained in a similar way as an oil in quantitative yield from the ester (X) of Example 2e).

NMR: δ 6.8–7.4 (m 7H), 4.7 (t 1H), 3.8 (s 3H), 3.7 (m 2H), 2.3 (s 3H), 2.0–2.3 (m 2H).

f) 3,3-Bis-(2-methoxy-5-methylphenyl)propanol (XXI) was obtained in a similar way in 98% yield from the ester (XI) of Example 2f). M.p. 89° (IPE).

$C_{19}H_{24}O_3$ (300.4) requires: C, 75.97; H, 8.05; O, 15.98, Found: C, 75.9; H, 8.02; O, 16.1.

g) 3-(2,5-Dibenzyloxyphenyl)-3-phenylpropanol (XXII) was obtained in a similar way in 88% yield from the ester (XII) of Example 2g). M.p. 78° (IPE).

$C_{29}H_{28}O_3$ (424.5) requires: C, 82.05; H, 6.65; O, 11.31, Found: C, 82.0; H, 6.62; O, 11.2.

h) 3,3-Bis-(2-benzyloxy-4-methylphenyl)propanol (XXIII) was obtained in a similar way as an oil in 93% yield from the ester (XIII) of Example 2h).

i) 3-(2,4-Dimethoxyphenyl)-3-phenylpropanol (XXIV) was obtained as a golden oil in 92% yield from the ester (XIV) of Example 2i).

NMR: δ 6.5–7.2 (m 8H), 4.5 (t 1H), 3.8 (s 6H), 3.6 (m 2H), 2.0–2.6 (m 3H).

j) 3,3-Bis-(2,4-dimethoxyphenyl)propanol (XXV) was obtained in a similar way from the impure ester (XV) of Example 2j). By NMR, the product contains about 20% of dimethyl resorcinol.

k) 3-(4-Fluorphenyl)-3-(2-methoxyphenyl)propanol (XXVI)

A Grignard reagent was prepared in the usual manner from o-bromoanisole (93.5 g, 0.5 mol) and magnesium (12 g, 0.5 mol) in 100 ml dry ether. A solution of p-fluorobenzaldehyde (62 g, 0.5 mol) in 100 ml ether was added dropwise to this solution. After about 1 h, the mixture was decomposed with $NH_4Cl$ and worked up, giving 100.6 g (87%) of 4-fluoro-2'-methoxy-diphenylmethanol. Recrystallization from IPE-PET gave white crystals, m.p. 88°.

$C_{14}H_{13}FO_2$ (232.3) requires: C, 72.40; H, 5.64, Found: C, 72.9; H, 5.75.

The obtained carbinol (46.2 g, 0.2 mol) in 600 ml ethanol was hydrogenated in the presence of 4 g of 5% Pd/C catalyst. After about 5–6 h, the reaction was complete and the mixture was worked up giving 40 g (93%) of 4-fluoro-2'-methoxy-diphenylmethane as a clear oil.

NMR: 6.8–7.2 (m 8H), 4.0 (s 2H), 3.8 (s 3H).

The obtained methane derivative (71 g, 0.33 mol) in 100 ml ether was added to a solution of $NaNH_2$ prepared in situ from sodium (8.5 g, 0.37 mol) in about 300 ml of $NH_3$. After about 1 h, a solution of ethylene oxide (17.5 g, 0.395 mol) in 75 ml ether was added dropwise. The mixture was stirred for 2 h, and most of the ammonia was then removed with a stream of air. Solid $NH_4Cl$ was then added, followed by the addition of water. The organic phase was separated, washed with water and 2N HCl, dried and evaporated, giving 81.5 g (95%) of the title compound. M.p. 61° (IPE-PET).

$C_{16}H_{17}FO_2$ (260.3) requires: C, 73.82; H, 6.58, Found: C, 74.1; H, 6.77.

l) 3-(5-Chloro-2-methoxyphenyl)-3-phenylpropanol

The ester from Example 2k) (91.5 g, 0.3 mol) in 500 ml dry ether was added dropwise under nitrogen to $LiAlH_4$ (11.4 g, 0.3 mol) in 200 ml dry ether. The mixture was stirred at room temperature overnight, then decomposed with 11 g water and 11 g 15% NaOH solution. Work up gave 72.5 g (87.5%) colourless oil. Recrystallization from IPE gave white crystals of the title compound, m.p. 80°.

$C_{16}H_{17}ClO_2$ (276.8) requires: C, 69.43; H, 6.19; Cl, 12.81, Found: C, 70.1; H, 6.44; Cl, 12.9.

EXAMPLE 4

Preparation of 3,3-diphenylpropyl-p-toluene sulphonates a) 3,3-Bis-(2-methoxyphenyl)propyl-p-toluene sulphonate (XXVII)

The propanol (XVII) of Example 3b) (35 g, 0.128 mol) in 100 ml chloroform containing 30 ml pyridine was cooled to about −10° and then treated with p-toluene sulphonyl chloride (29 g, 0.15 mol). After standing in the cooler (about +5° C.) overnight, the mixture was poured into ice-water, the organic phase was washed with water and cold 2N HCl, dried, and the solvent was distilled off at <50° C., giving a crude oil in quantitative yield. Recrystallization from IPE gave white crystals of low and indefinite m.p.

$C_{24}H_{26}O_5S$ (426.5) requires: C, 67.58; H, 6.14; S, 7.52, Found: C, 66.8; H, 6.22; S, 7.76.

b) 3(2-Methoxy-4-methylphenyl)-3-phenylpropyl-p-toluene sulphonate (XXXI) was obtained in quantitative yield from the propanol (XVI) of Example 3a).

c) 3-(2,3-Dibenzyloxyphenyl)-3-phenylpropyl-p-toluene sulphonate (XXVIII) was obtained in a similar way as a thick oil in 88% yield from the propanol (XVIII) of Example 3c).

d) 3-(2-Benzyloxyphenyl)-3-phenylpropyl-p-toluene sulphonate (XXIX) was obtained in i similar way in 98% yield from the propanol (XIX) of Example 3d).

e) 3-(2-Methoxy-5-methylphenyl)-3-phenylpropyl-p-toluene sulphonate (XXX) was obtained in quantitative yield from the propanol (XX) of Example 3e). M.p. 64° (IPE-PET).

$C_{23}H_{24}O_4S$ (396.5) requires: C, 69.67; H, 6.10; S, 8.09, Found: C, 69.8; H, 6.20; S, 7.85.

f) 3,3-Bis-(2-methoxy-5-methylphenyl)-propyl-p-toluene sulphonate (XXXII) was obtained in quantitative yield from the propanol (XXI) of Example 3f). M.p. 117° (acetone-PET).

$C_{26}H_{30}O_5S$ (454.5) requires: C, 68.7; H, 6.65; S, 7.05, Found: C, 68.8; H, 6.66; S, 7.11.

g) 3-(2,5-Dibenzyloxyphenyl)-3-phenylpropyl-p-toluene sulphonate (XXXIII) was obtained in a similar manner in quantitative yield from the propanol (XXII) of Example 3g).

h) 3,3-Bis-(2-benzyloxy-4-methylphenyl)-propyl-p-toluene sulphonate (XXXIV) was obtained in a similar way in 86% yield from the propanol (XXIII) of Example 3h).

i) 3-(2,4-Dimethoxyphenyl)-3-phenylpropyl-p-toluene sulphonate (XXXV) was in the same way obtained in 96% yield from the propanol (XXIV) of Example 3i).

j) 3,3-Bis-(2,4-dimethoxyphenyl)-propyl-p-toluene sulphonate (XXXVI) was obtained in the same manner from the propanol (XXV) of Example 3j). The product was contaminated with dimethyl resorcinol.

k) 3-(4-Fluorphenyl)-3-(2-methoxyphenyl)-propyl-p-toluene sulphonate (XXXVII) was obtained in a similar way in 88% yield from the propanol (XXVI) of Example 3k). M.p. 67° (IPE).

$C_{23}H_{23}FO_4S$ (414.5) requires: C, 66.65; H, 5.59; S, 7.74, Found: C, 67.1; H, 5.69; S, 7.78.

l) 3-(2-Methoxyphenyl)-3-phenylpropyl-p-toluene sulphonate (XLVIII)

A mixture of anisole (1080 g, 10 mol), benzyl alcohol (216 g, 2 mol) and p-toluene sulphonic acid (40 g) was refluxed for 2 h in an apparatus equipped with a water separator. Excess of anisole was then distilled off, the oily residue was dissolved in ether, washed with water and sodium carbonate, dried and fractionated, giving 304 g (77%) of a pale yellow oil, b.p. 115°–118°/0.4 Torr. By NMR, it is a 1:1 mixture of o-methoxy and p-methoxy diphenyl methane. This material was converted to a mixture of the corresponding propanols by reaction with ethylene oxide, as in the preparation of the propanol (XXVI) of Example 3k). This mixture of propanols was then converted as described above to a mixture of p-toluene sulphonates from which the title-compound could be isolated in 35% yield after two recrystallizations from IPE. M.p. 108°.

$C_{23}H_{24}O_4S$ (396.5) requires: C, 69.67; H, 6.10; S, 8.09, Found: C, 69.3; H, 6.00; S, 8.17.

m) 3-(5-Chloro-2-methoxyphenyl)-3-phenylpropyl-p-toluene sulphonate

The alcohol from Example 3l) (66 g, 0.24 mol) in 300 ml chloroform containing 75 ml pyridine was treated portionswise in the cold with p-toluene-sulphonyl chloride (55 g, 0.29 mol). The mixture was kept at 5° C. for 18 h, solvent was evaporated under vacuum at <50°, the residue was taken up in ether, washed with water and 2N HCl, dried and evaporated giving 100 g (97%) of a straw-yellow syrup. Recrystallization from IPE gave the title compound, m.p. 89°–90°.

$C_{23}H_{23}ClO_4S$ (430.96) requires: C, 64.10; H, 5.38; S, 7.44; Cl, 8.23, Found: C, 64.4; H, 5.45; S, 7.04; Cl, 8.17.

EXAMPLE 5

Preparation of tertiary 3,3-diphenylpropylamines a) N,N-Diisopropyl-3,3-bis-(2-methoxyphenyl)-propylamine (XXXVIII), hydrogen oxalate The tosylate (XXVII) of Example 4a) (42.6 g, 0.1 mol) in 100 ml acetonitrile and 100 g (1.0 mol) diisopropylamine was heated in a pressure bottle at 80° for 4–6 days. Volatile material was then evaporated, the residue was treated with excess of 2N NaOH and extracted with ether. The extract was washed with water and extracted with 2N HCl. This extract was washed with ether, basified, extracted with ether, washed with water, dried, decoloured, filtered, and evaporated, giving 24.0 g (68%) of a crude oil. This oil was converted to the oxalic acid salt by treating an acetone solution of the base with one equivalent of oxalic acid in acetone. M.p. 160°–161° (acetone).

$C_{25}H_{35}NO_6$ (445.6) requires: C, 67.39; H, 7.92; N, 3.14; O, 21.55, Found: C, 67.2; H, 8.22; N, 2.94; O, 21.9.

b) N,N-Diisopropyl-3-(2,3-dibenzyloxyphenyl)-3-phenylpropylamine (XXXIX)

The free base was obtained in the same way in 75% yield from the tosylate (XXVIII) of Example 4c).

NMR: 6.9–7.2 (m 18H), 5.0 (s 4H), 0.9 (d 12H).

c) N,N-Diisopropyl-3-(2-methoxy-5-methylphenyl)-3-phenylpropylamine (XL), hydrogenfumarate The free base was obtained in 69% yield from the tosylate (XXX) of Example 4e). It was converted to the fumaric acid salt in the usual manner. M.p. 176° (acetone).

$C_{27}H_{37}NO_5$ (455.7) requires: C, 71.17; H, 8.20; N, 3.07; O, 17.6, Found: C, 71.3; H, 8.27; N, 3.04; O, 17.9.

d) N,N-Diisopropyl-3-(2-methoxy-4-methylphenyl)-3-phenylpropylamine (XLI), hydrogenfumarate The free base was obtained in 25% yield from the tosylate (XXXI) of Example 4b). The fumaric acid salt had m.p. 147°–148° (acetone).

$C_{27}H_{37}NO_5$ (455.7) requires: C, 71.17; H, 8.20; N, 3.07; O, 17.6, Found: C, 71.3; H, 8.14; N, 3.00; O, 17.6.

e) N,N-Diisopropyl-3,3-bis-(2-methoxy-5-methylphenyl)propylamine (XLII), hydrochloride The free base was obtained in 78% yield from the tosylate (XXXII) of Example 4f). It was converted to the hydrochloride with ethereal HCl in the ususal manner. M.p. 163°–164° (acetone-ether).

$C_{25}H_{38}NO_2Cl$ (420.1) requires: C, 71.49; H, 9.12; N, 3.33; O, 7.61; Cl, 8.44, Found: C, 71.6; H, 9.08; N, 3.27; O, 7.93; Cl, 8.36.

f) N,N-Diisopropyl-3-(2,5-dibenzyloxyphenyl)-3-phenylpropylamine (XLIII)

The free base was obtained in 70% yield from the tosylate (XXXIII) of Example 4g).

NMR: δ 6.6–7.2 (m 18H), 5.0 (s 4H), 4.5 (t 1H), 1.0 (d 12H).

g) N,N-Diisopropyl-3,3-bis-(2-benzyloxy-4-methylphenyl)propylamine (XLIV)

The free base was obtained in 62% yield from the tosylate (XXXIV) of Example 4h).

NMR: δ 6.8–7.2 (m 16H), 4.8 (s 4H, t 1H), 0.9 (d 12H).

h) N,N-Diisopropyl-3-(2,4-dimethoxyphenyl)-3-phenylpropylamine (XLV)

The free base was obtained in 56% yield from the tosylate (XXXV) of Example 4i).

NMR: 6.5–7.3 (m 8H), 4.4 (t 1H), 3.8 (s 6H), 1.0 (d 12H).

i) N,N-Diisopropyl-3,3-bis-(2,4-dimethoxyphenyl)-propylamine (XLVI)

The free base was obtained in 34% yield from the tosylate (XXXVI) of Example 4j).

NMR: δ 6.5–7.3 (m 6H), 4.6 (t 1H), 3.9 (s 12H), 1.0 (d 12H).

j) N,N-Diisopropyl-3-(4-fluorophenyl)-3-(2-methoxyphenyl)propylamine XLVII)

The free base was obtained in 71% yield from the tosylate (XXXVII) of Example 4k).

k) N,N-Diisopropyl-3-(2-methoxyphenyl)-3-phenylpropylamine (XLIX), hydrogen fumarate The free base was obtained in 86% yield from the tosylate (XLVIII) of Example 4l) and was converted to the fumaric acid salt in the usual way. M.p. 134°–136° (acetone-IPE) or 163°–164° (methanol).

$C_{26}H_{36}NO_5$ (441.6) requires: C, 70.72; H, 7.99; N, 3.28; O, 18.12, Found: C, 70.8; H, 7.93; N, 3.28; O, 18.1.

l) N-(3-(2-Methoxyphenyl)-3-phenylpropyl)-2,2,6,6-tetramethylpiperidine (LXIV)

This compound was obtained in the same way in 54% yield from the tosylate (XLVIII) of Example 4l) and 2,2,6,6-tetramethylpiperidine. M.p. 100° (IPE).

$C_{25}H_{35}NO$ (365.6) requires: C, 82.14; H, 9.65; N, 3.83, Found: C, 82.0; H, 9.62; N, 3.57.

m) N,N-diisopropyl-3-(5-chloro-2-methoxyphenyl)-3-phenylpropylamine

The tosylate from Example 4m) (43.1 g, 0.1 mol) was heated for 4 days at 80° with diisopropylamine (50 g, 0.5 mol) in 100 ml acetonitrile, giving 23 g (64%) of crude title compound. By GC, it is at least 93% pure.

n) N-(3-(2-Benzyloxyphenyl)-3-phenylpropyl)-2,2,5,5-tetramethylpyrrolidine

This compound was similarly prepared from the tosylate (XXIX) of Example 4d) and 2,2,5,5-tetramethylpyrrolidine. It was obtained as a sticky oil, which was converted to the hydroxy analogue without further purification (Example 9ab)).

o) N-(3-(2-Benzyloxyphenyl)-3-phenylpropyl)-4-hydroxy-2,2,6,6-tetramethylpiperidine This compound was similarly prepared from the tosylate (XXIX) of Example 4d) and 4-hydroxy-2,2,6,6-tetramethylpiperidine, and it was obtained as a sticky oil which was converted to the hydroxy compound without further purification (Example 9ac)).

p) N-(2-Hydroxy-1,1-dimethylethyl)-3-(2-benxyloxyphenyl)-3-phenylpropylamine

This compound was similarly prepared from the tosylate (XXIX) of Example 4d) and 2-amino-2-methylpropanol. The solid product was crystallized from diisopropyl ether and melted at 103° C. It was used as start material in (Example 7p).

$C_{26}H_{31}NO_2$ (389.5) requires: C, 80.17; H, 8.02; N, 3.60; O, 8.22, Found: C, 80.0; H, 8.09; N, 3.69; O, 8.51.

q) N-(1-Adamantyl)-3-(2-benzyloxyphenyl)-3-phenylpropylamine

This compound was similarly prepared from the toyslate (XXIX) of Example 4d) and 1-aminoadamantane. It was used as start material in Example 7q). The hydrochloridesemihydrate was prepared in acetonitrile and melted at 225° C.

$C_{32}H_{37}NO.HCl.\frac{1}{2} H_2O$ (497.1) requires: C, 77.31; H, 7.91; N, 2.82; O, 4.83; Cl, 7.13, Found: C, 77.3; H, 8.23; N, 2.65; O, 5.04; Cl, 7.14.

EXAMPLE 6

Preparation of secondary 3,3-diphenylpropylamines a) N-tert.Butyl-3,3-bis-(2-methoxyphenyl)propylamine (L), hydrogen oxalate The tosylate (XXVII) of Example 4a) was heated with a large excess of tert.butylamine as described in Example 5, giving the free base in 78% yield, which was converted to the oxalic acid salt in the usual manner. M.p. 135°-136° (acetone-ether).

$C_{23}H_{31}NO_6$ (417.5) requires: C, 66.17; H, 7.48; N, 3.36; O, 22.99, Found: C, 65.6; H, 7.31N, 3.36; O, 23.4.

b) N-ter.Butyl-3-(2,3-dibenzyloxyphenyl)-3-phenylpropylamine (LI), hydrochloride The free base was obtained as above in 78% yield from the tosylate (XXVIII) of Example 4c). The HCl salt had m.p. 184°-185° (acetone-methanol-IPE).

$C_{33}H_{38}NO_2Cl$ (516.1) requires: C, 76.79; H, 7.42; N, 2.71; O, 6.20; Cl, 6.87, Found: C, 76.3; H, 7.30; N, 2.72; O, 6.42; Cl, 6.81.

c) N-tert.Butyl-3-(2-benzyloxyphenyl)-3-phenylpropylamine (LII), hydrogen oxalate The free base was obtained in 84% yield from the tosylate (XXIX) of Example 4d). The oxalic acid salt had m.p. 198° (acetone-ether).

$C_{28}H_{33}NO_5$ (463.6) requires: C, 72.54; H, 7.18; N, 3.02, Found: C, 71.8; H, 7.13; N, 2.95.

d) N-tert.Butyl-3-(2-methoxy-5-methyplenyl)-3-phenylpropylamine (LIII), hydrochloride The free base was obtained in 90% yield from the tosylate (XXX) of Example 4e). When treated with ethereal HCl, it gave a somewhat hygroscopic salt which seems to be associated with ¼ mol water. Mp. 171° ethanol-ether).

$C_{21}H_{29}NO.HCl.\frac{1}{4} H_2O$ (352.5) (requires): C, 71.55; H, 8.74; N, 3.97; O, 5.67; Cl, 10.06, Found: C, 71.8; H, 8.72; N, 4.05; O, 5.57; Cl, 10.1.

e) N-ter.Butyl-3-(2-methoxy-4-methylphenyl)-3-phenylpropylamine (LIV), hydrochloride The free base was obtained in quantitative yield from the tosylate (XXXI) of Example 4b). The HCl-salt had m.p. 138°-149° (methanol-isopropanol). It was associated with ¾ mol of water.

$C_{21}H_{30}NOCl.\frac{3}{4} H_2O$ (361.5) requires: C, 69.77; H, 8.80; N, 3.88; Cl, 9.81, Found: C, 69.8; H, 8.76; N, 3.93; Cl, 9.75.

f) N-ter.Butyl-3,3-bis-(2-methoxy-5-methylphenyl)-propylamine (LV), hydrochloride The free base was obtained in quantitative yield from the tosylate (XXXII) of Example 4f). The HCl-salt had m.p. 242° (acetone).

$C_{23}H_{34}NOCl$ (392.0) requires: C, 70.47; H, 8.74; N, 3.57; Cl, 9.05, Found: C, 70.2; H, 8.81; N, 3.46; Cl, 8.99.

g) N-tert.Butyl-3-(2,5-dibenzyloxyphenyl)-3-phenylpropylamine (LVI), hydrochloride The free base was obtained in 85% yield from the tosylate (XXXIII) of Example 4g). The HCl salt had m.p. 188° (ethanol-ether).

$C_{33}H_{38}NO_2Cl$ (516.1) requires: C, 76.79; H, 7.42; N, 2.71; O, 6.20; Cl, 6.87, Found: C, 77.2; H, 7.50; N, 2.64; O, 6.53; Cl, 6.85.

h) N-tert.Butyl-3,3-bis-(2-benzyloxy-4-methylphenyl)-propylamine (LVII), hydrochloride The free base was obtained in 94% yield from the tosylate (XXXIV) of Example 4h). The HCL-salt had m.p. 210° (acetone-ether).

$C_{35}H_{42}NO_2Cl$ (544.2) requires: C, 77.25; H, 7.78; N, 2.57; O, 5.89; Cl, 6.52, Found: C, 77.6; H, 7.82; N, 2.35; O, 6.08; Cl, 6.55.

i) N-tert.Butyl-3-(2,4-dimethoxyphenyl)-3-phenylpropylamine (LVIII), hydrochloride The free base was obtained in 84% yield from the tosylate (XXXV) of Example 4i). The HCl-salt had m.p. 196° (acetone-ethanol-ether).

$C_{21}H_{30}NO_2Cl$ (363.9) requires: C, 69.31; H, 8.31; N, 3.85; O, 8.79; Cl, 9.74, Found: C, 69.3; H, 8.44; N, 3.80; O, 8.89; Cl, 9.81.

j) N-tert.Butyl-3,3-bis-(2,4-dimethoxyphenyl)-propylamine (LIX), hydrochloride

The free base was obtained in 60% yield from the tosylate (XXXVI) of Example 4j). The HCl-salt had m.p. 251° (methanol-acetone).

$C_{23}H_{34}NO_4Cl$ (424.0) requires: C, 65.15; H, 8.08; N, 3.30; O, 15.09; Cl, 8.36, Found: C, 64.5; H, 8.06; N, 3.57; O, 15.3; Cl, 8.67.

k) N-tert.Butyl-3-(4-fluorophenyl)-3-(2-methoxyphenyl)-propylamine (LX), hydrochloride The free base was obtained in 89% yield from the tosylate (XXXVII) of Example 4k). The HCl-salt had m.p. 194° (ethanol-acetone).

$C_{20}H_{27}NOFCl$ (351.9) requires: C, 68.26; H, 7.73; N, 3.98; Cl, 10.08, Found: C, 68.9; H, 7.97; N, 4.01; Cl, 9.69.

l) N-tert.Butyl-3-(2-methoxyphenyl)-3-phenylpropylamine (LXI), hydrochloride

The free base was obtained in 88% yield from the tosylate (XLVIII) of Example 4l). The HCl-salt had m.p. 205°.

$C_{20}H_{28}NOCl$ (333.9) requires: C, 71.94; H, 8.45; N, 4.20; O, 4.79, Found: C, 71.9; H, 8.44; N, 4.67; O, 4.79.

m) N-(1,1-Dimethylpropyl)-3-(2-methoxy-5-methylphenyl)-3-phenylpropylamine (LXII), hydrochloride The free base was obtained in 95% yield from the tosylate (XXX) of Example 4e) and tert. amylamine. The HCl-salt had m.p. 188°–189° (ethanol-acetone).

$C_{22}H_{32}NOCl$ (362.0) requires: C, 73.00; H, 8.91; N, 3.87; O, 4.42; Cl, 9.80, Found: C, 73.4; H, 8.98; N, 3.83; O, 4.61; Cl, 9.51.

n) N-(1,1-Dimethylpropyl)-3,3-bis-(2-methoxy-5-methylphenyl)propylamine (LXIII), hydrochloride The free base was obtained in 94% yield from the tosylate (XXXII) of Example 4f) and tert.amylamine. The HCl-salt had m.p. 210° (ethanol-acetone).

$C_{24}H_{36}NO_2Cl$ (406.0) requires: C, 71.00; H, 8.94; N, 3.45; O, 7.88; Cl, 8.73, Found: C, 71.1; H, 9.01; N, 3.60; O, 7.92; Cl, 8.73.

o) N-tert.Butyl-3-(5-chloro-2-methoxyphenyl)-3-phenylpropylamine

The tosylate from Example 4m) (43.1 g, 0.1 mol) in 100 ml acetonitrile was treated with tert.butylamine (37 g, 0.5 mol) and the mixture was heated in a pressure bottle at 80° for 4 days. The usual work-up afforded 32 g (100%) crude title compound. The base in ether-acetone was treated with ethereal HCl giving the hydrochloride salt, m.p. 216°–218°.

$C_{20}H_{26}ClNO \cdot HCl$ (368.36) requires: C, 65.21; H, 7.39; N, 3.80; Cl, 19.25, Found: C, 65.1; H, 7.39; N, 3.90; Cl, 18.7.

EXAMPLE 7

Preparation of tertiary 3,3-diphenylpropylamines from secondary amines a) N-Methyl-N-tert.butyl-3-(2-methoxyphenyl)-3-phenylpropylamine (LXV), hydrochloride A mixture of the secondary amine (LXI) of Example 6l) (29.7 g, 0.1 mol), formic acid (13.8 g, 0.3 mol), and 37% formaldehyde solution (12.5 g, 0.12 mol) was refluxed for 18–24 h. The mixture was then cooled, basified with NaOH, and extracted with ether. The extract was washed with water, dried and evaporated, giving 29.3 g (94%) of a crude oil. The HCl-salt was prepared from ethereal HCl in the usual way, m.p. 199°.

$C_{21}H_{30}NOCl$ (347.9) requires: C, 72.49; H, 8.69; N, 4.03; Cl, 10.19, Found: C, 71.9; H, 8.79; N, 4.23; Cl, 10.1.

b) N-Methyl-N-tert.butyl-3-(2-methoxy-5-methylphenyl)-3-phenylpropylamine (LXVI), hydrochloride The free base was obtained in the same way in 89% yield from the amine (LIII) of Example 6d). The HCl-salt had m.p. 161° (acetone).

$C_{22}H_{32}NOCl$ (362.0) requires: C, 73.00; H, 8.91; N, 3.87; O, 4.42; Cl, 9.08, Found: C, 73.0; H, 8.96; N, 3.94; O, 4.59; Cl, 9.77.

c) N-Methyl-N-tert.butyl-3,3-bis-(2-methoxyphenyl)propylamine (LXVII), hydrochloride The free base was obtained in 96% yield from the amine (L) of Example 6a). The HCl-salt had m.p. 187°–190° (acetone-ether).

$C_{22}H_{33}NOCl$ (378.0) requires: C, 69.91; H, 8.54; N, 3.71; O, 8.47; Cl, 9.38, Found: C, 69.9; H, 8.56; N, 3.53; O, 8.93; Cl, 8.92.

d) N-Methyl-N-tert.butyl-3-(2-methoxy-4-methylphenyl)-3-phenylpropylamine (LXVIII)

The free base was obtained in 96% yield from the amine (LIV) of Example 6e). M.p. 64° (IPE).

$C_{22}H_{31}NO$ (325.5) requires: C, 81.17; H, 9.60; N, 4.30; O, 4.92, Found: C, 81.0; H, 9.83; N, 4.15; O, 5.03.

e) N-Methyl-N-tert.butyl-3,3-bis-(2-methoxy-5-methylphenyl)propylamine (LXIX)

The free base was obtained in 97% yield from the amine (LV) of Example 6f). M.p. 95° (IPE).

$C_{24}H_{35}NO_2$ (370.0) requires: C, 78.00; H, 9.55; N, 3.79; O, 8.66, Found: C, 78.1; H, 9.57; N, 3.70; O, 8.80.

f) N-Methyl-N-tert.butyl-3-(4-fluorophenyl)-3-(2-methoxyphenyl)propylamine (LXX), hydrochloride The free base was obtained in 82% yield from the amine (LX) of Example 6k). The HCl-salt had m.p. 218° (ethanol-acetone).

$C_{21}H_{29}NOClF$ (365.9) requires: C, 68.93; H, 7.99; N, 3.83; Cl, 9.69, Found: C, 69.0; H, 7.97; N, 3.95; Cl, 9.60.

g) N-(1,1-Dimethylpropyl)-N-methyl-3-(2-methoxy-5-methylphenyl)-3-phenylpropylamine (LXXI), hydrochloride The free base was obtained in 98% yield from the amine (LXII) of Example 6m). The HCl-salt had m.p. 176°–177° (acetone).

$C_{23}H_{34}NOCl$ (376.0) requires: C, 73.47; H, 9.11; N, 3.73; Cl, 9.43, Found: C, 73.4; H, 9.15; N, 3.73; Cl, 9.41.

h) N-(1,1-Dimethylpropyl)-N-methyl-3,3-bis-(2-methoxy-5-methylphenyl)propylamine (LXXII), hydrochloride The free base was obtained in 89% yield from the amine (LXIII) of Example 6n). The HCl-salt had m.p. 147° (acetone-ether).

$C_{25}H_{37}NO_2Cl$ (420.1) requires: C, 71.49; H, 9.12; N, 3.34; O, 7.62; Cl, 8.44, Found: C, 70.8; H, 9.20; N, 3.63; O, 7.74; Cl, 8.42.

i) N-Methyl-N-tert.butyl-3-(2,4-dimethoxyphenyl)-3-phenylpropylamine (LXXIII)

This compound was obtained as an oil in quantitative yield from the amine (LVIII) of Example 6i).

NMR: 6.5–7.3 (m 8H), 4.3 (t 1H), 3.8 (s 6H), 2.3 (s 3H), 1.0 (s 9H).

j) N-Methyl-N-tert.butyl-3-(2,5-dibenzyloxyphenyl)-3-phenylpropylamine (LXXIV)

This was obtained as an oil in 95% yield from the amine (LVI) of Example 6g).

k) N-Methyl-N-tert.butyl-3,3-bis-(2-benzyloxy-4-methylphenyl)propylamine (LXXV), hydrochloride The free base was obtained in 92% yield from the amine (LVII) of Example 6k). The HCl-salt had m.p. 170°–171° (acetone-ether).

$C_{36}H_{44}NO_2Cl$ (558.2) requires: C, 77.46; H, 7.95; N, 2.51; O, 5.73; Cl, 6.35, Found: C, 77.6; H, 7.86; N, 2.42; O, 5.89; Cl, 6.31.

l) N-Methyl-N-tert.butyl-3,3-bis-(2,4-dimethoxyphenyl)propylamine (LXXVI), hydrochloride The free base was obtained in 96% yield from the amine (LIX) of Example 6j). The HCl-salt had m.p. 180°–190° and seems to be associated with ¼ mol of water.

$C_{24}H_{36}NO_4Cl \cdot ¼ H_2O$ (447.0) requires: C, 64.48; H, 8.34; N, 3.13; O, 16.11; Cl, 7.93, Found: C, 64.5; H, 8.27; N, 3.02; O, 16.2; Cl, 8.19.

m) N-Methyl-N-tert.butyl-3-(2,3-dibenzyloxyphenyl)-3-phenylpropylamine (LXXVII)

This was obtained as an oil in 98% yield from the amine (LI) of Example 6b).

NMR: δ 6.9–7.3 (m 18H), 2.1 (s 3H), 1.0 (s 9H).

n) N-Methyl-N-tert.butyl-3-(2-benzyloxyphenyl)-3-phenylpropylamine (LXXVIII)

This was obtained as an oil in 97% yield from the amine (LII) of Example 6c).

NMR: 6.9–7.3 (m 14H), 5.0 (s 4H), 4.5 (t 1H), 2.2 (s, 3H), 0.9 (s, 9H).

o) N-Methyl-N-tert.butyl-3-(5-chloro-2-methoxyphenyl)-3-phenylpropylamine

The secondary amine from Example 6o) (25.3 g, 0.076 mol) was refluxed for 18 h with formic acid (9.2 g, 0.2 mol) and 35% formaldehyde solution (8.5 g, 0.1 mol). Work-up gave 25.6 g, (97.5%) crude base. This was dissolved in acetone and treated with an equimolar quantity of oxalic acid in acetone giving beige crystals of the title compound, hydrogen oxalate, m.p. 165°.

$C_{21}H_{28}ClNO \cdot C_2H_2O_4$ (436.0) requires: C, 63.37; H, 6.94; N, 3.21; Cl, 8.13, Found: C, 62.7; H, 6.83; N, 3.10; Cl, 7.97.

p) N-(2-Hydroxy-1,1-dimethylethyl)-N-methyl-3-(2-benzyloxyphenyl)-3-phenylpropylamine This compound was similarly prepared from the compound of Example 5p). It was obtained as a sticky oil which was converted to the free hydroxy compound of Example 9ad).

q) N-1-Adamantyl-N-methyl-3-(2-benzyloxyphenyl)-3-phenylpropylamine

This compound was similarly prepared from the compound of Example 5q). It was obtained as a sticky oil which was converted to the free hydroxy compound of Example 9ae) without further purification.

EXAMPLE 8

Preparation from olefinic precursors a) N-tert.butyl-3-(2,6-dimethoxyphenyl)-3-hydroxy-3-phenylpropylamine (LXXIX)

A solution of diisopropylamine (10.1 g, 0.1 mol) in dry ether (100 ml) was cooled to −10°. A solution of butyl lithium in hexane (65 ml, 0.1 mol) was added, and the mixture was stirred at −10° for 20 min. A solution of N-ethylidene-tert.butylamine (10 g, 0.1 mol) in dry ether (100 ml) was added and the solution was stirred at 0° for 20 min. After cooling to −30° a solution of 2,6-dimethoxybenzophenone (24.1 g, 0.1 mol) in dry ether (100 ml), containing 30 ml THF, was added. The mixture was then stirred at ambient temperature for 20 h and hydrolized with water. The organic phase was washed with water, dried and evaporated, giving 32 g (94%) of N-(3-(2,6-dimethoxyphenyl)-3-hydroxy-3phenylpropylidene)tert.butylamine as an oil.

This oil was dissolved in absolute ethanol (250 ml), the solution was cooled to −5°, and NaBH$_4$ (5.7 g, 0.15 mol) was added portionwise. The mixture was stirred at 0° for ½ h, then at ambient temperature for 3 h. Most of the solvent was distilled off in vacuum, the residue was treated with water, extracted with ether, washed with water, and extracted with 2N HCl. The extract was washed with ether, basified with NaOH, extracted with ether, dried and evaporated, giving 30 g of the title amine.

The HCl-salt had m.p. 203°–204° (acetone-ether) and seems to be associated with ¼ mol of water.

$C_{21}H_{29}NO_3 \cdot HCl \cdot \frac{1}{4} H_2O$ (384.5) requires: C, 65.60; H, 8.01; N, 3.64; O, 13.52, Found: C, 65.9; H, 8.11; N, 3.64; O, 13.7.

b) N-tert.Butyl-3-(2,6-dimethoxyphenyl)-3-phenyl-2-propene-1-amine (LXXX)

The above amine from step a) (21 g, 0.061 mol) was added to 6.3N H$_2$SO$_4$ (20 ml, 0.126 mol). The mixture was stirred on a boiling water bath for 2 h, cooled, basified, and extracted with ether. The extract was washed, dried and evaporated, giving 17.8 g, (90%) of the title olefin as a clear oil. The HCl-salt had m.p. 220°–22°, and was associated with ¼ mol of water.

$C_{21}H_{27}NO_2 \cdot HCl \cdot \frac{1}{4} H_2O$ requires: C, 68.82; H, 7.86; N, 3.82; O, 9.82; Cl, 9.68, Found: C, 68.8; H, 7.89; N, 3.92; O, 9.81; Cl, 9.44.

c) N-Methyl-N-tert.butyl-3-(2,6-dimethoxyphenyl)-3-phenylpropylamine (LXXXI), hydrogen fumarate hydrogen fumarate The olefinic amine from step b) (16.3 g, 0.05 mol) in methanol (250 ml) containing 0.5 g of a 10% Pd/C catalyst, was hydrogenated at ambient temperature and pressure. The mixture was then filtered through Celaton, the filtrate was taken to dryness, giving 16.3 g (100%) of N-tert.butyl-3-(2,6-dimethoxyphenyl)-3-phenylpropylamine. The HCl-salt had m.p. 244° (ethanol).

$C_{21}H_{29}NO_2 \cdot HCl$ (363.9) requires: C, 69.31; H, 8.31; N, 3.85; O, 8.79; Cl, 9.74, Found: C, 69.3; H, 8.29; N, 3.83; O, 9.27; Cl, 9.75.

The above secondary amine, as the free base, was methylated with formaldehydeformic acid as described in Example 7, giving the tertiary amine in 96% yield. The fumaric acid salt had m.p. 185°–190° (acetone).

$C_{26}H_{35}NO_6$ (457.6) requires: C, 68.25; H, 7.71; N, 3.06; O, 20.95, Found: C, 67.8; H, 7.59; N, 3.05; O, 21.6.

EXAMPLE 9

Removal of O-protective groups a) N,N-Diisopropyl-3-(2-hydroxyphenyl)-3-phenylpropylamine (LXXXII), hydrochloride The amine (XLIX) of Example 5k) (20.8 g, 0.064 mol) in methylene chloride (150 ml) was cooled below 0°. A 1N solution of BBr$_3$ in CH$_2$Cl$_2$ (64 ml, 0.064 mol) was then added dropwise, the solution was then kept in the cooler (5°) for 2–5 days, and volatile material was distilled off at <50°. The residual syrup was basified, extracted with ether, the extract was washed with water, dried and evaporated, giving a viscous syrup. The HCl-salt had m.p. 222° (methanol-ether), yield 31%.

$C_{21}H_{29}NO \cdot HCl$ (347.9) requires: C, 72.49; H, 8.69; N, 4.03; O, 4.60; Cl, 10.19, Found: C, 72.0; H, 8.72; N, 3.74; O, 5.06; Cl, 10.3.

The following compounds were obtained in the same way.

b) N-(3-(2-Hydroxyphenyl)-3-phenylpropyl)-2,2,6,6-tetramethylpiperidine (LXXXIII), hydrogen fumarate From the amine (LXIV) of Example 5l). Crude yield 78%. M.p. fumaric acid salt=indefinite.

$C_{28}H_{37}O_5$ (467.6) requires: C, 71.9; H, 7.91; N, 3.00; O, 17.1, Found: C, 71.8; H, 8.41; N, 3.01; O, 16.6.

c) N,N-Diisopropyl-3-(2-hydroxy-5-methylphenyl)-3-phenylpropylamine (LXXXIV), hydrochloride From the amine (XL) of Example 5c). Crude yield 85%. HCl-salt, m.p. 209°–210° (acetone-ether).

$C_{22}H_{31}NO \cdot HCl \cdot \frac{1}{4} H_2O$ (366.5) requires: C, 72.09; H, 8.95; N, 3.82; O, 5.46; Cl, 9.67, Found: C, 72.3; H, 8.95; N, 3.71; O, 5.68; Cl, 9.61.

d) N-Methyl-N-tert.butyl-3-(2-hydroxy-5-methylphenyl)-3-phenylpropylamine (LXXXV), hydrochloride From the amine (LXVI) of Example 7b). Crude yield 100%. HCl-salt, m.p. >260° (ethanol).

$C_{21}H_{29}NO \cdot HCl$ (347.4) requires: C, 72.49; H, 8.69; N, 4.03; Cl, 10.19, Found: C, 72.7; H, 8.58; N, 3.81; Cl, 10.95.

e) N,N-Diisopropyl-3,3-bis-(2-hydroxyphenyl)-propylamine (LXXXVI), hydrochloride From the amine (XXXVIII) of Example 5a). Crude yield 57%. HCl-salt, m.p. 257° (ethanol-ether).

$C_{21}H_{29}NO_2 \cdot HCl$ (363.9) requires: C, 69.31; H, 8.31; N, 3.85; O, 8.79; Cl, 9.74, Found: C, 69.3; H, 8.37; N, 3.95; O, 9.23; Cl, 9.40.

f) N-Methyl-N-tert.butyl-3,3-bis-(2-hydroxyphenyl)-propylamine (LXXXVII), hydrochloride From the amine (LXVII) of Example 7c). Crude yield 100%, m.p. 190°. HCl-salt, m.p. 252° (ethanol).

$C_{20}H_{27}NO_2 \cdot HCl$ (349.9) requires: C, 68.65; H, 8.06; N, 4.00; Cl, 10.13, Found: C, 68.4; H, 8.06; N, 4.17; Cl, 9.59.

g) N,N-Diisopropyl-3-(2-hydroxy-4-methylphenyl)-3-phenylpropylamine (LXXXVIII), hydrochloride From the amine (XLI) of Example 5d). Crude yield 90%. HCl-salt, m.p. 217° (ethanol).

$C_{22}H_{31}NO \cdot HCl \cdot \frac{1}{4} H_2O$ (366.5) requires: C, 72.09; H, 8.96; N, 3.82; O, 5.46; Cl, 9.67, Found: C, 72.3; H, 8.91; N, 3.93; O, 5.27; Cl, 9.46.

h) N,N-Diisopropyl-3,3-bis-(2-hydroxy-5-methylphenyl)propylamine (LXXXIX), hydrochloride From the amine (XLII) of Example 5e). Crude yield 93%, m.p. 166°. HCl-salt, m.p. 220° (ethanol).

$C_{23}H_{33}NO_2 \cdot HCl$ (392.0) requires: C, 70.47; H, 8.74; N, 3.57; Cl, 9.05, Found: C, 70.6; H, 8.78; N, 3.71; Cl, 8.93.

i) N-Methyl-N-tert.butyl-3,3-bis-(2-hydroxy-5-methylphenyl)propylamine (XC), hydrochloride From the amine (LXIX) of Example 7e). Crude yield 79%, m.p. 199°–201° (IPE). HCl-salt, m.p. 220° (acetone).

$C_{22}H_{31}NO_2 \cdot HCl$ (378.0) requires: C, 69.91; H, 8.54; N, 3.71; O, 8.47; Cl, 9.38, Found: C, 69.9; H, 8.70; N, 3.75; O, 8.81; Cl, 9.15.

j) N-Methyl-N-tert.butyl-3-(2-hydroxy-4-methylphenyl)-3-phenylpropylamine (XCI), hydrochloride From the amine (LXVIII) of Example 7d). Crude yield 100%. HCl-salt, m.p. 240° (ethanol).

$C_{21}H_{29}NO \cdot HCl$ (347.9) requires: C, 72.49; H, 8.69; N, 4.03; O, 4.60; Cl, 10.19, Found: C, 72.51 H, 8.75; N, 4.06; O, 4.90; Cl, 10.1.

k) N,N-Diisopropyl-3-(4-fluorophenyl)-3-(2-hydroxyphenyl)propylamine (XCII), hydrochloride From the amine (XLVII) of Example 5j). Crude yield 72%. HCl-salt, m.p. 183° (acetone-ethanol).

$C_{21}H_{27}FNO \cdot HCl$ (364.9) requires: C, 69.12; H, 7.73; N, 3.83, Found: C, 69.1; H, 8.09; N, 3.82.

l) N,N-Diisopropyl-3-(2,4-dihydroxyphenyl)-3-phenylpropylamine (XCIII), hydrochloride From the amine (XLV) of Example 5h). Crude yield 31%. HCl-salt, m.p. 205°–210° (ethanol-acetone-ether).

$C_{21}H_{29}NO_2 \cdot HCl$ (363.9) requires: C, 69.31; H, 8.31; N, 3.85; O, 8.79; Cl, 9.74, Found: C, 69.5; H, 8.33; N, 3.72; O, 8.91; Cl, 9.87.

m) N-(1,1-Dimethylpropyl)-N-methyl-3,3-bis-(2-hydroxy-5-methylphenyl)propylamine (XCIV), hydrochloride From the amine (LXXII) of Example 7h). Crude yield 100%, m.p. 190°–195°. HCl-salt, m.p. 235°–240° (ethanol-acetone-ether).

$C_{23}H_{33}NO_2 \cdot HCl$ (392.0) requires: C, 70.47; H, 8.74; N, 3.57; O, 8.16; Cl, 9.05, Found: C, 70.0; H, 8.96; N, 3.54; O, 8.11; Cl, 9.19.

n) N-Methyl-N-tert.butyl-3-(2,4-dihydroxyphenyl)-3-phenylpropylamine (XCV), hydrobromide From the amine (LXXIII) of Example 7i). Crude yield 78%, m.p. 260°. HBr-salt, m.p. >260° (ethanol).

$C_{20}H_{25}NO_2 \cdot HBr$ (394.4) requires: C, 60.9; H, 7.16; N, 3.55; O, 8.11; Br, 20.27, Found: C, 60.8; H, 7.18; N, 3.29; O, 8.38; Br, 20.2.

o) N,N-Diisopropyl-3,3-bis-(2,4-dihydroxyphenyl)-propylamine (XCVI), hydrochloride From the amine (XLVI) of Example 5i). The HCl-salt, consisting of an amorphous brown powder, did not give a satisfactory elemental analysis because of incomplete combustion.

p) N-Methyl-N-tert.butyl-3,3-bis-(2,4-dihydroxyphenyl)propylamine (XCVII), hydrochloride From the amine (LXXVI) of Example 7l). Crude yield 87%, m.p. 260°. The HCl-salt did not give a satisfactory elemental analysis because of incomplete combustion.

q) N,N-Diisopropyl-3-(2,5-dihydroxyphenyl)-3-phenylpropylamine (XCVIII), hydrochloride The amine (XLIII) of Example 5f) in the form of the free base (32 g, 0.063 mol) in methanol (500 ml) containing 5 g of a 5% Pd/C catalyst was hydrogenated at ambient temperature and pressure. After 2 h the reaction was complete. The mixture was filtered, the filtrate was taken to dryness, the residue was dissolved in acetone and treated with ethereal HCl, giving 19.8 g (87%) of a crude salt, m.p. 260°. Recrystallization from methanol gave white crystals, m.p. 260°.

$C_{21}H_{29}NO_2 \cdot HCl \cdot \frac{1}{4} H_2O$ (368.6) requires: C, 68.44; H, 8.36; N, 3.80; O, 9.77; Cl, 9.62, Found: C, 68.4; H, 8.40; N, 3.60; O, 10.3; Cl, 9.42.

The following compounds were prepared in the same way.

r) N-Methyl-N-tert.butyl-3-(2,5-dihydroxyphenyl)-3-phenylpropylamine (XCIX), hydrochloride From the amine (LXXIV) of Example 7j). Crude yield 90%. HCl-salt, m.p. >270° (methanol-water).

$C_{20}H_{27}NO_2 \cdot HCl$ (349.9) requires: C, 68.65; H, 8.06; N, 4.00; O, 9.14; Cl, 10.13, Found: C, 68.9; H, 8.02; N, 3.93; O, 9.60; Cl, 10.5.

s) N,N-Diisopropyl-3,3-bis-(2-hydroxy-4-methylphenyl)propylamine (C), hydrochloride From the amine (XLIV) of Example 5g). Crude yield 100%. HCl-salt, m.p. 253° (methanol-ether).

$C_{23}H_{33}NO_2 \cdot HCl$ (392.0) requires: C, 70.47; H, 8.74; N, 3.57; O, 8.16; Cl, 9.05, Found: C, 70.5; H, 8.74; N, 3.55; O, 8.47; Cl, 8.03.

t) N-Methyl-N-tert.butyl-3,3-bis-(2-hydroxy-4-methylphenyl)propylamine (CI), hydrochloride From the amine (LXXV) of Example 7k). Crude yield 97%, a yellow powder. HCl-salt, m.p. 260° (methanol-acetone).

$C_{22}H_{31}NO_2 \cdot HCl$ (378.0) requires: C, 69.91; H, 8.54; N, 3.71; O, 8.47; Cl, 9.38, Found: C, 69.9; H, 8.68; N, 3.67; O, 8.85; Cl, 9.24.

u) N,N-Diisopropyl-3-(2,3-dihydroxyphenyl)-3-phenylpropylamine (CII), hydrochloride From the amine (XXXIX) of Example 5b). Crude yield 100%. HCl-salt, m.p. 174°–176° (acetone).

$C_{21}H_{29}NO_2 \cdot HCl$ (363.9) requires: C, 69.31; H, 8.31; N, 3.85; O, 8.79; Cl, 9.74, Found: C, 69.5; H, 8.33; N, 3.66; O, 9.37; Cl, 9.63.

w) N-Methyl-N-tert.butyl-3-(2,3-dihydroxyphenyl)-3-phenylpropylamine (CIII), hydrochloride From the amine (LXXVII) of Example 7m). Crude yield 100%, a white powder. HCl-salt, m.p. 209°–210°, slow heating, (methanol-acetone).

$C_{20}H_{27}NO_2 \cdot HCl \cdot \frac{1}{2} H_2O$ (358.9) requires: C, 66.92; H, 8.14; N, 3.90; O, 11.14; Cl, 9.88, Found: C, 66.9; H, 8.12; N, 3.76; O, 11.8; Cl, 9.74.

x) N-Methyl-N-tert.butyl-3-(2-hydroxyphenyl)-3-phenylpropylamine (CIV), hydrochloride From the amine (LXXVIII) of Example 7n). Crude yield 100%. HCl-salt, m.p. 255° (acetone-ether).

$C_{20}H_{27}NO \cdot HCl$ (333.9) requires: C, 71.94; H, 8.45; N, 4.20; Cl, 10.62, Found: C, 71.9; H, 8.43; N, 4.01; Cl, 10.5.

y) N-Methyl-N-tert.butyl-3-(2,6-dihydroxyphenyl)-3-phenylpropylamine (CV), hydrochloride From the amine (LXXXI) of Example 8c) with $BBr_3$, in low yield. HCl-salt, m.p. 170° (ethanol-ether).

$C_{20}H_{27}NO_2 \cdot HCl \cdot \frac{1}{2} H_2O$ (358.9) requires: C, 66.93; H, 8.14; N, 3.40; O, 11.14; Cl, 9.87, Found: C, 67.4; H, 8.28; N, 3.63; O, 10.9; Cl, 9.99.

z) N,N-Diisopropyl-3-(5-chloro-2-hydroxyphenyl)-3-phenylpropylamine

The base from Example 5m) (11.7 g, 0.032 mol) was treated with pyridine (7.6 g, 0.096 mol) and conc. HCl (13 g). The mixture was taken to dryness in vacuum and the residue was heated in an oil-bath at 205°-215° for 1½ h. The melt was cooled somewhat, water was added, the mixture was digested in a boiling water bath and cooled. 2N HCl was added, the salt was filtered off, washed with 2N HCl and dried, giving 11.0 g (90%) white salt m.p. 200°. Recrystallization from acetone gave the hydrochloride of the title compound, m.p. 202°-203°.

$C_{21}H_{28}ClNO \cdot HCl$ (382.4) requires: C, 65.96; H, 7.64; N, 3.66; Cl, 18.54, Found: C, 66.0; H, 7.88; N, 3.63; Cl, 18.3.

aa) N-Methyl-N-tert.butyl-3-(5-chloro-2-hydroxyphenyl)-3-phenylpropylamine

The free base from Example 7o) (10.5 g, 0.03 mol) was treated with pyridine (7.0 g, 0.09 mol) and conc. HCl (12 g). The mixture was taken to dryness in vacuum and the residue was heated in an oil-bath at 205°-215° for 1½ h. The melt was cooled somewhat, excess of 2N NaOH was added, the mixture was extracted with ether, the extract was washed with water, dried and evaporated giving 7.5 g (88%) crude syrup. This was dissolved in ether and treated with ethereal HCl giving 8 g (83%) of hydrochloride salt. Recrystallization from acetone-2N HCl gave the hydrochloride of the title compound, m.p. 260°.

$C_{20}H_{26}ClNO \cdot HCl$ (368.4) requires: C, 65.21; H, 7.39; N, 3.80; Cl, 19.25, Found: C, 65.0; H, 7.30; N, 3.73; Cl, 18.9.

ab) N-(3-(2-Hydroxyphenyl)-3-phenylpropyl)-2,2,5,5-tetramethylpyrrolidine

The crude amine from Example 5n) was hydrogenolysed as described in Example 9q). The free amine was obtained as an oil which was converted to the hydrochloride and crystallized from 2-propanol. M.p. 250° C.

$C_{23}H_{31}NO \cdot HCl$ (374.0) requires: C, 73.86; H, 8.63; N, 3.75; O, 4.28; Cl, 9.48, Found: C, 73.8; H, 8.71; N, 3.59; O, 4.80; Cl, 9.45.

ac) N-(3-(2-Hydroxyphenyl)-3-phenylpropyl)-4-hydroxy-2,2,6,6-tetramethylpiperidine The benzyloxy compound from Example 5o) was hydrogenolysed as described in Example 9q). The free base was converted to the hydrochloride semihydrate which was crystallized from acetone. The compound melts with decomposition at about 150° C.

$C_{24}H_{33}NO_2 \cdot HCl \cdot \frac{1}{2} H_2O$ (413.0) requires: C, 69.79; H, 8.54; N, 3.39; O, 9.68; Cl, 8.58, Found: C, 70.0; H, 8.67; N, 3.47; O, 9.98; Cl, 8.13.

ad) N-(2-Hydroxy-1,1-dimethylethyl)-N-methyl-3-(2-hydroxyphenyl)-3-phenylpropylamine The benzyloxy compound from Example 7p) was hydrogenolysed as described in Example 9q). The amine, obtained as a glassy mass, was converted to the hydrochloride which was obtained as an amorphous solid on precipitation from ethanol with ether.

$C_{20}H_{27}NO_2 \cdot HCl$ (349.9) requires: C, 68.65; H, 8.06; N, 4.00; O, 9.15; Cl, 10.13, Found: C, 68.25; H, 8.18; N, 3.98; O, 9.12; Cl, 10.0.

ae) N-1-Adamantyl-N-methyl-3-(2-hydroxyphenyl)-3-phenylpropylamine

The benzyloxy compound from Example 7q) was hydrogenolysed as described in Example 9q). The free hydroxyamine was obtained as a glassy mass. It was dissolved in anhydrous ether and treated with an excess of hydrogen chloride in ether. The hydrochloride precipitated as a powder which decomposed at about 220° C.

$C_{26}H_{33}NO \cdot HCl$ (412.0) requires: C, 75.79; H, 8.32; N, 3.40; O, 3.88; Cl, 8.61, Found: C, 75.3; H, 8.01; N, 3.22; O, 3.45; Cl, 8.96.

EXAMPLE 10

Reduction of amides a) N,N-Diisopropyl-3-(2-methoxy-5-methylphenyl)-3-phenylpropylamine 3-(2-Methoxy-5-methylphenyl)-3-phenylpropionic acid (12.8 g, 0.05 mol) (J. D. Simpson & H. Stehphen, J. Chem. Soc. 1956 1382) and thionyl chloride (50 ml) are heated on a water bath for 3 h. The excess of thionyl chloride is distilled off under reduced pressure. The remaining crude 3-(2-methoxy-5-methylphenyl)3-phenylpropionyl chloride is dissolved in 50 ml of dichloromethane and added dropwise to a stirred solution of diisopropylamine (20.2 g, 0.20 mol) in 200 ml of dichloromethane at about 0° C. The solution is left for 2 h, the solvent is distilled off and the remaining material is treated with water. The solid product consisting of N,N-diisopropyl-3-(2-methoxy-5-methylphenyl)-3-phenylpropionamide is filtered off, dried and added in small portions to a stirred suspension of lithium aluminium hydride (6.0 g, 0.16 mol) in dry ether (700 ml). The mixture is refluxed for 2 days. Excess of hydride is destroyed by the careful addition of water, the ether layer is separated and dried with anhydrous sodium sulfate. After filtration the solution is added to a solution of excess fumaric acid in ether. The precipitated salt is collected and crystallized from 2-propanol. The hydrogen fumarate melts at 176° C.

b) N-Methyl-N-tert.butyl-3-(2-methoxy-5-methylphenyl)-3-phenylpropylamine was similarly prepared. The hydrochloride melts at 161° C.

EXAMPLE 11 a) N-Methyl-N-tert.butyl-3-(5-chloro-2-hydroxyphenyl)-3-phenylpropylamine

A solution of chlorine (7,1 g, 0,10 mol) in acetic acid (500 ml) is added dropwise to a stirred solution of N-methyl-N-tert.butyl-3-(2-hydroxyphenyl)-3 -phenylpropylamine (29.7 g. 0.10 mol) in acetic acid (200 ml) with stirring. After 2 h the solvent is distilled off under reduced pressure and the crude hydrochloride left is recrystallized from 2-propanol. Melting point 260° C.

b) N,N-Diisopropyl-3-(5-chloro-2-hydroxyphenyl)-3-phenylpropylamine is similarly prepared. The hydrochloride melts at 202°-3° C.

EXAMPLE 12

Separation of (+)- and (−)-enantiomers (±)-N,N-Diisopropyl-3-(2-hydroxyphenyl)-3-phenylpropylamine (31.1 g, 0.10 mol) is dissolved in 300 ml of ethanol. A solution of L-(+)-tartaric acid (15.0 g, 0.10 mol) in 400 ml of ethanol is added. The mixture is heated a few minutes in a boiling water bath and seeded with crystals obtained by cooling and scratching a small sample of the main solution. The mixture is chilled at about 4° C. over-night whereupon the crystalline precipitate is filtered off, washed with cold ethanol and recrystallized repeatedly from ethanol. The pure (−)-N,N-diisopropyl-3-(2-hydroxyphenyl)-3-phenylpropylamine hydrogen L-(+)-tartrate thus obtained has $[\alpha]_D^{20} -10.6°$ (c=5% in methanol). The free amine is obtained by alkalisation of an aqueous solution, extraction into ether, drying and evaporation of the solvent. Sticky oil, $[\alpha]_D^{20} -5.4°$ (c=5% in methanol).

(+)-N,N-Diisopropyl-3-(2-hydroxyphenyl)-3-phenylpropylamine is similarly prepared using D-(−)-tartaric acid. The hydrogen-D-(−)tartrate has $[\alpha]_D^{20} +10.0°$. The free amine has $[\alpha]_D^{20} +5.6°$, both measured as 5% solutions in methanol.

EXAMPLE 13 (CONTINUATION OF EXAMPLE 1)

Preparation of 4-phenyl-3,4-dihydrocoumarins g) 4-(2-Methoxyphenyl)6-methyl-3,4-dihydrocoumarin (CIV)

A mixture of 2-methoxycinnamic acid (178 g, 1.0 mol), p-cresol (108 g, 1.0 mol), and p-touenesulphonic acid monohydrate (47.5 g, 0.25 mol) was stirred on a boiling water-bath for about 2 h during which time the system was evacuated with a waterpump to remove formed water. The solid was then broken up and washed copiously with water. The granular material was then stirred with a large volume of saturated NaHCO₃ solution containing some 10% acetone. The product was filtered off, washed dried and recrystallised from acetone affording 167 g (62,5%) white crystals of the desired lactone, m.p. 140°.

$C_{17}H_{16}O_3$ (268.3) requires: C, 76.10; H, 6.01; O, 17.89, Found: C, 76.0; H, 5.97; O, 17.9.

h) 6-Chloro-4-(2-methoxyphenyl)-3,4-dihydrocoumarin (CVII) was prepared in a similar way in 49% yield from 2-methoxycinnamic acid and p-chlorophenol, the reaction temperature being 130° in this case. M.p. 172°–173° (acetone).

$C_{16}H_{13}O_3$ (288.7) requires: C, 66.56; H, 4.54; O, 16.62, Found: C, 66.8; H, 4.45; O, 16.5.

EXAMPLE 14 (CONTINUATION OF EXAMPLE 2)

Preparation of 3,3-diphenylpropionic acid esters l) Methyl-3-(2-methoxyphenyl)-3-(2-methoxy-5-methylphenyl)propionate (CVIII) was obtained as an oil in 75% yield from the lactone CVI of Example 13g in the manner described for the ester VI of Example 2a).

m) Methyl-3-(5-chloro-2-methoxyphenyl)-3-(2methoxyphenyl)propionate (CIX) was obtained as an oil in the same way in 97% yield from the lactone CVII of Example 13.

EXAMPLE 15 (CONTINUATION OF EXAMPLE 3)

Preparation of 3,3-diphenylpropanols m) 3-(5-Chloro-2-methoxyphenyl)-3-(2-methoxyphenyl)propanol (CX) was obtained in 84% yield from the ester CIX of Example 14m in the manner described for the propanol XVI of Example 3a), except that the reduction was carried out in toluene with a 10% molar excess of a 3.4M toluenic solution of sodium bis(2-methoxyethoxy)aluminium hydride (SMEAH) instead of LiAlH₄. M.p. 70°–72°(IPE).

n) 3-(2-Methoxyphenyl)-3-(2-methoxy-5-methylphenyl)propanol (CXI) was obtained in the same way in quantitive yield from the ester CVIII of Example 14l). The product consisted of a golden oil of 89% purity according to GC.

EXAMPLE 16 (CONTINUATION OF EXAMPLE 4)

Preparation of 3,3-diphenylpropyl-p-toluenesulphonates n) 3-(2-Methoxyphenyl)-3-(2-methoxy-5-methylphenyl)propyl-p-toluene-sulphonate (CXII) was prepared in the same way as the tosylate XXVII of Example 4a) in quantitative yield from the propanol CXI of Example 15n) using CH₂Cl₂ as solvent instead of chloroform. M.p. 101° (ether/IPE).

$C_{25}H_{28}O_5S$ (440.57) requires: C, 68.16; H, 6.41; S, 7.28, Found: C, 68.3; H, 6.51; S, 7.20.

o) 3-(5-Chloro-2-methoxyphenyl)-3-(2-methoxyphenyl)propyl-p-toluenesulphonate (CXIII) was obtained in the same way in quantitative yield from the propanol CX of Example 15m. M.p. 97°–98° (acetone-/IPE).

$C_{24}H_{25}ClO_5S$ (460.92) requires: C, 62.54; H, 5.47; S, 6.94; Cl, 7.69, Found: C, 63.0; H, 5.65; S, 6.95; Cl, 7.70.

EXAMPLE 17 (CONTINUATION OF EXAMPLE 5)

Preparation of tertiary 3,3-diphenylpropylamines r) N,N-Diisopropyl-3-(5-chloro-2-methoxyphenyl)-3-(2-methoxyphenyl)propylamine (CXIV) was obtained as an oil in 94% yield from the tosylate CXIII of Example 16o) in the manner described for the amine XXXVIII of Example 5a). Purity by GC=99.9%.

s) N,N-Diisopropyl-3-(2-methoxyphenyl)-3-(2-methoxy-5-methylphenyl)propylamine (CXV) was obtained in the same way in 49% crude yield from the tosylate CXV of Example 16n). After chromatographic purification on an Si-gel 60 column (eluation with light petroleum), the product (oil) had a purity of 100% according to GC.

t) N-[(2-Benzyloxy-5-methyl)-3-phenyl]-2,2,5,5-tetramethylpyrrolidine (CXVI) was prepared from 3-(2-benzyloxy-5-methyl)-3-phenylpropyl tosylate and 2,2,5,5-tetramethylpyrrolidine following the directions given in Example 5a). It was obtained as a sticky oil which was converted to the free hydroxy compound of Example 20aj).

EXAMPLE 18 (CONTINUATION OF EXAMPLE 6)

Preparation of secondary 3,3-diphenylpropylamines p) N-tert.Butyl-3-(5-chloro-2-methoxyphenyl)-3-(2-methoxyphenyl)propylamine (CXVII) was prepared in quantitative yield from the tosylate CXIII of Example 16o) in the manner described for the amine L of Example 6a). The HCl-salt had m.p. >260°.

$C_{21}H_{28}ClNO_2.HCl$ (398.38) requires: C, 63.3; H, 7.34; N, 3.52; Cl, 17.80, Found: C, 63.2; H, 7.46; N, 3.49; Cl, 17.4.

q) N-tert.Butyl-3-(2-methoxyphenyl)-3-(2-methoxy-5-methylphenyl)propylamine (CXVIII) was obtained in a similar way in 89% crude yield from the tosylate CXII of Example 16n). The HCl-salt had m.p. 225°.

$C_{22}H_{31}O_2N.HCl$ (377.97)

Requires: C, 69.91; H, 8.54; N, 3.71; Cl, 9.38; O, 8.47, Found: C, 69.8; H, 8.73; N, 3.60; Cl, 9.45; O, 8.79.

EXAMPLE 19 (CONTINUATION OF EXAMPLE 7)

Preparation of tertiary 3,3-diphenylpropylamines from secondary amines r) N-Methyl-N-tert.butyl-3-(5-chloro-2-methoxyphenyl)-3-(2-methoxyphenyl)propylamine (CXIX) was prepared in 89% yield from the amine CXVII of Example 18p) in the manner described for the amine LXI of Example 7a). The HCl-salt was prepared by treating an acetonic solution of the free base with conctrated hydrochloric acid. M.p. 130°.

$C_{22}H_{30}ClO_2N.HCl.H_2O$ (430.42)

Requires: C, 61.39; H, 7.74; N, 3.25; Cl, 16.47, Found: C, 62.0; H, 7.93; N, 3.26; Cl, 16.5.

s) N-Methyl-N-tert.butyl-3-(2-methoxyphenyl)-3-(2-methoxy-5-methylphenyl)propylamine (CXX) was prepared in a similar way in 98% yield from the amine CXVIII of Example 18q). The free base (oil) had a purity of 96% by GC.

EXAMPLE 20 (CONTINUATION OF EXAMPLE 9)

Removal of O-proptective groups af) N,N-Diisopropyl-3-(2-hydroxyphenyl)-3-(2-hydroxy-5-methylphenyl)propylamine (CXXI)

The amine CXV from Example 17s) (26.5 g, 0.072 mol) in methanol was treated with a slight excess of concentrated hydrochloric acid. The mixture was taken to dryness in vacuum, pyridinium chloride (25.4 g, 0.22 mol) was added and the mixture was then heated at 200°-205° for 1½ h. The mixture was cooled to about 80°, acetone (20 g) was added followed by addition of little water. The salt was filtered off, washed with diluted HCl and dried. Recrystallisation from absolute ethanol/ether gave 17.5 g (64.3%) of a white salt, m.p. >250°. Purity by GC=100%.

$C_{22}H_{31}NO_2.HCl$ (377.97) Requires: C, 69.91; H, 8.54; N, 3.71; O, 8.47; Cl, 9.38, Found: C, 69.8; H, 8.65; N, 3.57; O, 8.76; Cl, 9.51.

ag) N,N-Diisopropyl-3-(5-chloro-2-hydroxyphenyl)-3-(2-hydroxyphenyl)propylamine (CXXII was prepared in the same way in 37% yield from the amine CXIV of Example 17r). The HCl-salt had m.p. 214° (ethanol).

$C_{21}H_{28}NO_2.HCl$ (398.38) Requires: C, 63.31; H, 7.34; N, 3.52; O 8.03; Cl, 17.80, Found: C, 63.1; H, 7.34; N, 3.40; O, 8.15; Cl, 17.8.

ah) N-Methyl-N-tert.butyl-3-(2-hydroxyphenyl)-3-(2-hydroxy-5-methylphenyl)propylamine (CXXIII) was prepared in the same way in 30% yield from the amino CXX of Example 19s). The HCl-salt had m.p. 240° (acetone).

$C_{21}H_{29}NO_2.HCl$ (363.94) requires: C, 69.3; H, 8.31; N, 3.58; Cl, 9.74, Found: C, 69.0; H, 8.35; N, 3.65; Cl, 9.76.

ai) N-Methyl-N-tert.butyl-3-(5-chloro-2-hydroxyphenyl)-3-(2-hydroxyphenyl)propylamine (CXXIV) was prepared in the same way in 24% yield from the amine CXIX of Example 19r). M.p. >250°.

$C_{20}H_{26}ClNO_2.HCl$ (384.36) requires: C, 62.50; H, 7.08; N, 3.65; Cl, 18.45, Found: C, 62.5; H, 7.09; N, 3.63; Cl, 18.4.

aj) N-[3-(2-Hydroxy-5-methylphenyl)-3-phenylpropyl]-2,2,5,5-tetramethylpyrrolidine (CXXV) was obtained when the O-benzylated amine CXVI of Example 17t) was hydrogenolyzed as described in Example 9q. The hydrochloride melts at 240°.

$C_{24}H_{34}ClNO$ (388.0) requires: C, 74.29; H, 8.83; N, 3.61; Cl, 19.14, Found: C, 73.9; H, 8.90; N, 3.52; Cl, 9.48.

EXAMPLE 21 (CONTINUATION OF EXAMPLE 10)

Reduction of amides

N,N-Diisopropyl-3-(2-methoxyphenyl)-3-phenylpropionamine

N,N-Diisopropyl-3-(2-methoxyphenyl)-3-phenylpropionamide was obtained as o pale yellow oil in quantitative yield from 3-(2-methoxyphenyl)-3-phenylpropionic acid in the manner described for the amide of Example 10a). This amide (27 g, 0.08 mol) in toluene (50 g) was added dropwise under r.t. to a 3.4M toluenic solution of SMEAH (50 g, 0,17 mol) diluted with an equal weight of toluene. The mixture was stirred at 60°-70° for 2 h, cooled, treated with excess od 2N NaOH. The organic phase was separated, washed with water and extracted with 2N HCl. The acidic extract was washed with ether, basified, extracted with ether, dried and evaporated giving 17.1 g (66%) free base. This was dissolved in acetone (75 ml) and treated with 6.6 g fumaric acid dissolved in methanol, affording 20 g of the fumaric acid salt, m.p. 163°-164°.

$C_{22}H_{31}ON.C_4H_4O_4$ (441.58) requires: C, 70.72; H, 7.99; N, 3.17; O, 18.12, Found: C, 70.7; H, 7.96; N, 3.13; O, 18.0.

EXAMPLE 22

Separation of (+)- and (−)-enantiomers (+)-N,N-Diisopropyl-3-(2-hydroxy-5-methylphenyl)-3-phenylpropylamine hydrogen tartrate The racemic amine (LXXXVIII of Example 9g) (48.8 g, 0.15 mol) was dissolved in 500 ml of 95% ethanol and mixed with a solution of L(+)-tartaric acid (22.5 g, 0.15 mol) in 500 ml of ethanol. The mixture was left over night at +4°. The precipitated salt was collected by filtration and washed with ethanol and ether. The yield of crude salt with $[\alpha]_{546}^{25}+29.5°$ (C 5%, methanol) was 34,3 g. Two recrystallisations from ethanol afforded 21.8 g with $[\alpha]_{546}^{25}+36.0°$.

$C_{26}H_{37}NO_7$ requires: C, 65.66; H, 7.84; N, 2.95; O, 23.55, Found: C, 65.9; H, 8.06; N, 2.90; O, 23.5.

(−)-N,N-Diisopropyl-3-(2-hydroxy-5-methylphenyl)-3-phenylpropylamine hydrogen D(−)-tartrate was similarly prepared using D(−)-tartaric acid.

$[\alpha]_{546}^{25}$ −35.8°.

Found: C, 65.6; H, 8.00; N, 2.83; O, 23.6.

Several of the compounds according to the invention were tested with regard to anti-cholinergic, anti-noradrenaline, and anti-calcium effects, toxicity and effect on the heart rate. The test procedures are described below, and the test results are reported in Table 1. For comparison purposes the testing also included the commercially available drug terodiline and a structurally similar compound, N,N-dimethyl-3-(2-methoxyphenyl)-3-phenylpropylamine, disclosed as an antidepressant in U.S. Pat. No. 3,446,901, GB-A-1.169.944, and GB-A-1.169.945. The test results clearly show that the compounds according to the invention are superior to the known compounds especially as regards selectively between the desired anti-cholinergic activity and the undesired side-effects.

a) Anticholinergic activity on isolated urinary bladder

Male guinea-pigs, weighing 250–350 g, were killed by a blow on the head and exsanguinated. The urinary bladders were quickly removed and placed in $Na^+$-Krebs, in which they were kept throughout the dissection procedure. The bladders were dissected free from adherent fat and connective tissue before they were cut open by an incision on each side from the base towards apex. The mucosa was carefully removed with a pair of scissors. Four strips, approximately 3–5 mm long were prepared by cutting in a parallel direction to the longitudinal muscle fibers, on each half of the bladder.

The bladder strips were immediately mounted vertically in 5 ml organ baths containing $Na^+$-Krebs solution aerated with carbogene gas to maintain the pH at about 7.4. The temperature, 37° C., was thermostatically controlled by a Lauda MS3 thermostatic circulator. The preparations were suspended between two hooks, one of which was connected to a Grass Instruments FTO3 force transducer. The isomeric tension of the preparations was recorded by a Grass polygraph model 79D. The resting tension was applied to approximately 5 mN. The strips were allowed to stabilize for at least 45 minutes. During this period the resting tension was adjusted to 5 mN and the preparations were repeatedly washed.

In the preliminary experiments concentration-effect curves for carbachol (carbamylcholin chloride) were studied, in order to determine a suitable agonist concentration for inhibition studies with antagonist. The carbachol concentration chosen, $3 \times 10^{-6}M$, produced a submaximal contractant response (70%). In the inhibition studies, the strips were contracted with carbachol ($3 \times 10^{-6}M$) every 15 minutes. The strips were washed three times after every agonist addition. This procedure was repeated until a reproducible contractant response was observed. A variation of about 10% for three subsequent contractions was accepted as reproducible.

Initially each antagonist was tested in a concentration of $10^{-6}M$, on two bladder-strips from different guinea-pigs. When a reproducible response with $3 \times 10^{-6}M$ carbachol was obtained, the strips were incubated with the antagonist for 15 minutes before the next carbachol was added. If the antagonist produced more than 50% inhibition of the response to carbachol, a complete concentration-inhibition curve was also made. In the complete inhibition curves, the strips were then incubated for 60 minutes with a fixed concentration of the antagonist before the next addition of carbachol. The effect of the antagonists was calculated as per cent inhibition of the mean of the initial agonist-induced contractions. To generate concentration-inhibition curves the antagonists were studied in 6–8 concentrations and for each concentration a fresh preparation was used, i.e. the strips were only exposed to the antagonist once before they were discarded.

b) Antagonistic effect to noradrenaline and calcium on the portal vein Preparation of isolated portal vein from rat Animals: Albino, male rats, weighing about 200 g.
Bath volume: 5 ml
Buffer: $Na^+$-Krebs, modified by K. E. Andersson
Temperature: 37° C.
Gas: Carbogene (93.5% $O_2$ + 6.5% $CO_2$)
Muscle tension: 0.5 g The rat is killed by a blow on the neck and decapitated. The abdomen is opened, the vein is dissected free from fat, cut open longitudinally and mounted in an organ bath. Changes in isometric tension is registered by a force displacement transducer, connected to an amplifier and a writing oscillograph.

Noradrenaline-antagonism on portal vein

Doses: Noradrenaline $3 \times 10^{-7}M$

The chosen doses give about 70% of maximal response. The agonist is added to the bath at 10-minutes intervals. When reproducible contractions are obtained a fixed concentration of the test substance is added to the bath. After an incubation period of 10 minutes noradrenaline is added. The next concentration of the test substance is added when the original response of the agonist is obtained.

The antagonistic effect of the substance is calculated as per cent inhibition of the mean response by three preceding doses of the agonist.

Ca-antagonistic effect on portal vein 10 mM $K^+$-solution is added to the Krebs buffer to stabilize the spontaneous myogenic activity of the vein. The amplitude of the muscle contractions is measured. The test substance is added to the bath in cumulative doses until total inhibition is obtained.

c) Histamine-antagonism on isolated ileum
Preparation of isolated ileum from guinea pigs
Animals: Guinea pigs of both sexes, weighing about 350 g.
Bath volume: 5 ml
Buffer: $Na^+$-Krebs, modified by K. E. Andersson
Temperature: 37° C.
Gas: Carbogene (93.5% $O_2$ + 6.5% $CO_2$)
Muscle tension: 0.5 g The guinea pig is killed by a blow on the neck and decapitated. The abdomen is opened and about 2 cm of the ileum is cut off about 15 cm above the ileocaecal junction. The piece of ileum is washed with buffer and mounted in an organ bath. Changes in isometric tension is recorded by a force displacement transducer, connected to an amplifier and a writing oscillograph.

Dose: $5 \times 10^{-7}M$ of histamine.

The chosen dose of histamine gives about 70% of maximal response. The agonist is added to the bath at 3-minutes intervals. When reproducible contractions are obtained a fixed concentration of the test substance is added to the bath. After an incubation period of 2–10 minutes a new contraction is induced by histamine. The next concentration of the test substance is added when the original response of the agonist is obtained.

The agonistic effect of the test substance is calculated as per cent inhibition of the mean response by three preceding doses of histamine.

d) Acute toxicity in mice

The antagonists to be tested were dissolved in 0.9% NaCl. If they were not soluble in 0.9% NaCl they were dissolved in double distilled water. The solutions were prepared on the day of the experiment.

Procedure

White male mice, 25 g, were placed in a mouse holder. The tested compounds were given as i.v. bolus doses in one of the four tail-veins, with a volume of 0.01 ml/g mouse. Each substance concentration was given to a group of four mice. 4–5 different concentrations of the antagonists were made and tested.

The acute lethal dose ($LD_{11}$) was the lowest concentration of the anticholinergic drug where 4 mice of 4 tested died within 5 minutes after an i.v. bolus dose.

$LD_{50}$-interval: The $LD_{50}$-interval was between the highest dose where 4 mice survived and the lowest dose where 4 mice died within 5 minutes after an i.v. bolus dose.

e) Effect on heart rate in conscious rat

The animal is slightly anaestetized by ether and an infusion cannula is inserted into a tail vein. While still asleep the rat is placed in a simple device, made of a coarse, somewhat elastic net fixing the rat in a constant position. Electrodes are attached to the extremities and connected to an ECG-pulse pre-amplifier and a Grass polygraph. By recording the ECG, the heart rate can then be determined.

Before any substance is given the animal has regained consciousness and the heart rate has been constant for at least 15 minutes.

The substance is injected, i.v. in the infusion cannula and flushed with physiological saline.

ECG is recorded 0.25, 0.5, 1, 2, 3 and 5 minutes after completed injection and then every 5 minutes until the original heart rate is obtained.

TABLE 1

| Substance | Antichol. effect $IC_{50}$ (M) | Anti-N.A. effect $IC_{50}$ (M) | Anti-Ca effect $IC_{50}$ (M) | Anti-HI effect $IC_{50}$ (M) | Acute toxicity i.v. mg/kg | Lethal dose mg/kg | Effect on heart rate threshold dose mg/kg |
|---|---|---|---|---|---|---|---|
| Terodiline (prior art) | $5.2 \times 10^{-7}$ | $2.4 \times 10^{-6}$ | $10^{-5}$ | $4 \times 10^{-6}$ | 15–20 | 20 | 1–3 |
| GB-A-1.169.944 (antidepressant) | $1.2 \times 10^{-6}$ | $4.4 \times 10^{-6}$ | $2.1 \times 10^{-5}$ | $3.7 \times 10^{-7}$ | 10–15 | 15 | |
| 1 Racemate | $1.8 \times 10^{-8}$ | $10^{-5}$ | $1.5 \times 10^{-5}$ | $7 \times 10^{-6}$ | 10–20 | 20 | 1–3 |
| 1a (+)-isomer of 1 | $1.8 \times 10^{-8}$ | | | | | | |
| 1b (−)-isomer of 1 | $1.4 \times 10^{-8}$ | | | | | | |
| 2 | $1.5 \times 10^{-7}$ | $3.5 \times 10^{-6}$ | $9 \times 10^{-6}$ | | 10–20 | 20 | |

TABLE 1-continued

| Substance | Antichol. effect IC$_{50}$ (M) | Anti-N.A. effect IC$_{50}$ (M) | Anti-Ca effect IC$_{50}$ (M) | Anti-HI effect IC$_{50}$ (M) | Acute toxicity i.v. mg/kg | Lethal dose mg/kg | Effect on heart rate threshold dose mg/kg |
|---|---|---|---|---|---|---|---|
| 3: 2-OCH$_3$-phenyl, phenyl -CH-CH$_2$-CH$_2$-N(CH(CH$_3$)$_2$)$_2$ | 2.4 × 10$^{-7}$ | 3.6 × 10$^{-6}$ | >10$^{-4}$ | | 3–10 | 10 | |
| 4: 2-OH-4-CH$_3$-phenyl, phenyl -CH-CH$_2$-CH$_2$-N(CH(CH$_3$)$_2$)$_2$ | 1.5 × 10$^{-8}$ | 5.5 × 10$^{-6}$ | 6 × 10$^{-6}$ | 10$^{-5}$ | 30–40 | 40 | |
| 4a. (+)-isomer of 4-tartrate | 1.3 × 10$^{-8}$ | | 6.5 × 10$^{-6}$ | | 10–20 | 20 | |
| 4b. (−)-isomer of 4-tartrate | 1.3 × 10$^{-6}$ | | 6 × 10$^{-6}$ | | 10–20 | 20 | |
| 5: 2-OH-phenyl, 2-OH-phenyl -CH-CH$_2$-CH$_2$-N(C(CH$_3$)$_3$)(CH$_3$) | 4.9 × 10$^{-9}$ | 3.8 × 10$^{-5}$ | 3 × 10$^{-5}$ | 10$^{-5}$ | 30–45 | 45 | 1–3 |
| 6: 2,4-di-OH-phenyl, phenyl -CH-CH$_2$-CH$_2$-N(C(CH$_3$)$_3$)(CH$_3$) | 2.0 × 10$^{-7}$ | 3 × 10$^{-5}$ | 6.5 × 10$^{-5}$ | 1.3 × 10$^{-5}$ | >20 | >20 | |
| 7: 2,5-di-OH-phenyl, phenyl -CH-CH$_2$-CH$_2$-N(CH(CH$_3$)$_2$)$_2$ | 1.9 × 10$^{-8}$ | 5 × 10$^{-5}$ | 6.5 × 10$^{-5}$ | 3 × 10$^{-6}$ | 30–50 | 50 | |
| 8: 2,5-di-OH-phenyl, phenyl -CH-CH$_2$-CH$_2$-N(C(CH$_3$)$_3$)(CH$_3$) | 3.1 × 10$^{-8}$ | 5 × 10$^{-5}$ | >5 × 10$^{-5}$ | 7 × 10$^{-6}$ | >6 | >6 | |

TABLE 1-continued

| Substance | Antichol. effect IC$_{50}$ (M) | Anti-N.A. effect IC$_{50}$ (M) | Anti-Ca effect IC$_{50}$ (M) | Anti-HI effect IC$_{50}$ (M) | Acute toxicity i.v. mg/kg | Lethal dose mg/kg | Effect on heart rate threshold dose mg/kg |
|---|---|---|---|---|---|---|---|
| 9 [2-hydroxyphenyl-phenyl-CH–CH$_2$–CH$_2$–N(C(CH$_3$)$_3$)(CH$_3$)] | $1.6 \times 10^{-8}$ | $5 \times 10^{-5}$ | $2.5 \times 10^{-5}$ | $1.2 \times 10^{-6}$ | | 20 | |
| 10 [2-methoxyphenyl-phenyl-CH–CH$_2$–CH$_2$–N(2,2,6,6-tetramethylpiperidinyl)] | $6.2 \times 10^{-8}$ | $4 \times 10^{-6}$ | $7 \times 10^{-6}$ | $2.5 \times 10^{-6}$ | | | |
| 11 [4-methyl-2-hydroxyphenyl-phenyl-CH–CH$_2$–CH$_2$–N(CH(CH$_3$)$_2$)$_2$] | $1.0 \times 10^{-8}$ | $5.5 \times 10^{-6}$ | $10^{-5}$ | $2.5 \times 10^{-6}$ | 10–20 | 20 | |
| 12 [2,6-dihydroxyphenyl-phenyl-CH–CH$_2$–CH$_2$–N(C(CH$_3$)$_3$)(CH$_3$)] | $4.7 \times 10^{-7}$ | | $2.3 \times 10^{-5}$ | $8.0 \times 10^{-6}$ | 15–30 | 30 | |
| 13 [bis(2-hydroxyphenyl)-CH–CH$_2$–CH$_2$–N(C(CH$_3$)$_2$)(CH(CH$_3$)$_2$)] | $9.0 \times 10^{-9}$ | $3 \times 10^{-5}$ | $1.5 \times 10^{-5}$ | $2 \times 10^{-5}$ | 5–10 | 10 | |

EXAMPLE A

Preparation of tablets

| Ingredients | mg/tablet |
|---|---|
| 1. Compound 1 in Table 1 | 2.0 |
| 2. Cellulose, microcrystalline | 57.0 |
| 3. Calcium hydrogen phosphate | 15.0 |
| 4. Sodium starch glycolate | 5.0 |
| 5. Silicon dioxide, colloidal | 0.25 |
| 6. Magnesium stearate | 0.75 |
| | 80.0 mg |

The compound 1 according to the invention is mixed with ingredients 2, 3, 4 and 5 for about 10 minutes. The magnesium stearate is then added, the resultant mixture being mixed for about 5 minutes and then compressed into tablet form with or without filmcoating.

EXAMPLE B

Preparation of capsules

| Ingredients | mg/capsule |
|---|---|
| 1. Compound 1 in Table 1 | 2 |
| 2. Lactose | 186 |
| 3. Corn starch | 20 |
| 4. Talc | 15 |
| 5. Magnesium stearate | 2 |
| | 225 mg |

The compound 1 according to the invention is mixed with ingredients 2 and 3 and then milled. The resulting mixture is then mixed with ingredients 4 and 5 and then filled into capsules of appropriate size.

We claim:

1. 3,3-Diphenylpropylamines of formula I

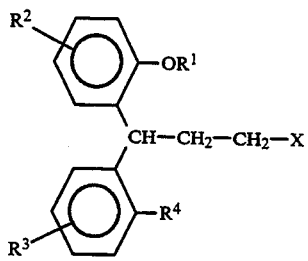

wherein $R^1$ signifies hydrogen or methyl, $R^2$, $R^3$ and $R^4$ independently signify hydrogen, methyl, methoxy, hydroxy, carbamoyl, sulphamoyl or halogen, and X represents a tertiary amino group of formula II

wherein each of $R^5$ and $R^6$ independently signifies $C_{1-6}$alkyl, which may be joined to form a non-aromatic ring having no hetero atom other than the amine nitrogen and each of which may carry a hydroxy substituent, or adamantyl, and wherein $R^5$ and $R^6$ together contain at least four carbon atoms, their salts with physiologically acceptable acids and, when the compounds can be in the form of optical isomers, the racemic mixture and the individual enantiomers.

2. 3,3-Diphenylpropylamines according to claim 1, wherein at least one of $R^5$ and $R^6$ is $C_{1-6}$alkyl comprising a branched carbon chain.

3. 3,3-Diphenylpropylamines according to claim 1, wherein X signifies any of the following groups a)–f), each of which may carry a hydroxy substituent:

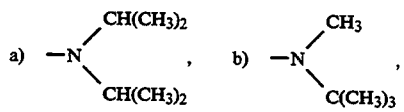

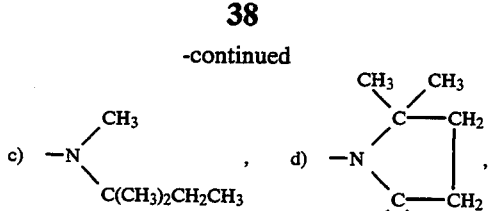

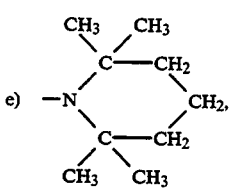

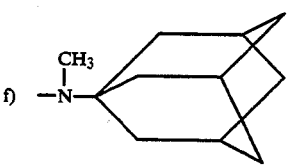

4. 3,3-Diphenylpropylamines according to claim 1, selected from the group consisting of the following compounds, their salts with physiologically acceptable acids and, where possible, their racemates and individual enantiomers: N,N-diisopropyl-3-(2-hydroxy-5-methylphenyl)-3-phenylpropylamine,N-methyl-N-tert-.butyl-3-(2-hydroxyphenyl)-3-phenylpropylamine, N-methyl-N-tert.butyl-3-(2,4-dihydroxyphenyl)-3-phenylpropylamine, N-methyl-N-tert.butyl-3,3-bis-(2-hydroxyphenyl)propylamine, N,N-diisopropyl-3,3-bis-(2-hydroxyphenyl)propylamine, N,N-diisopropyl-3-(2,5-hydroxyphenyl)propylamine, N,N-diisopropyl-3-(2,5-dihydroxyphenyl)-3-phenylpropylamine, N-methyl-N-tert.butyl-3-(2,5-dihydroxyphenyl)-3-phenylpropylamine,N-N-diisopropyl-3-(2-methoxyphenyl)-3-phenylpropylamine, N-2,2,6,6-tetramethylpiperdine-,(+)-N,N-diisopropyl-3-(2-hydroxy-5-methylphenyl)-3-phenylpropylamine, and N,N-diisopropyl-3-(5-chloro-2-hydroxyphenyl)-3-phenylpropylamine.

5. A pharmaceutical composition comprising a 3,3-diphenylpropylamine according to claim 1 and a compatible pharmaceutical carrier.

6. The 3,3-diphenylpropylamines of claim 1 being (+)-isomers.

7. The pharmaceutical composition of claim 5 wherein the 3,3-diphenylpropylamine is present in effective anticholinergic amount.

* * * * *

UNITED STATES PATENT AND TRADEMARK OFFICE
CERTIFICATE OF CORRECTION

| | | |
|---|---|---|
| PATENT NO. | : 5,382,600 | Page 1 of 1 |
| APPLICATION NO. | : 07/810185 | |
| DATED | : January 17, 1995 | |
| INVENTOR(S) | : Jönsson et al. | |

It is certified that error appears in the above-identified patent and that said Letters Patent is hereby corrected as shown below:

Claim 4, col. 38, line 39:
"N-2,2,6,6-tetramethylpiperdine-" should read
--N-(3-(2-methoxyphenyl)-3-phenylpropyl)-2,2,6,6-tetramethylpiperidine--

Signed and Sealed this

Eighteenth Day of July, 2006

JON W. DUDAS
*Director of the United States Patent and Trademark Office*